United States Patent [19]

Nathanson

[11] Patent Number: 5,366,975
[45] Date of Patent: Nov. 22, 1994

[54] INVERTEBRATE PHENYLETHANOLAMINE TRANSPORTER AND THE USE THEREOF

[75] Inventor: James A. Nathanson, Wellesley, Mass.

[73] Assignee: The General Hospital Corporation, Boston, Mass.

[21] Appl. No.: 997,698

[22] Filed: Dec. 28, 1992

Related U.S. Application Data

[63] Continuation-in-part of Ser. No. 814,877, Jan. 2, 1992, abandoned, which is a continuation-in-part of Ser. No. 721,322, Jul. 1, 1991, abandoned.

[51] Int. Cl.$^5$ .............................................. A01N 43/60
[52] U.S. Cl. ..................................... 514/255; 514/653
[58] Field of Search ................. 514/255, 653; 544/397; 210/764

[56] References Cited

U.S. PATENT DOCUMENTS

| | | | |
|---|---|---|---|
| 2,554,736 | 5/1951 | Haefliger et al. | 260/239 |
| 3,244,748 | 4/1966 | Tishler et al. | 260/562 |
| 3,271,451 | 9/1966 | Tishler et al. | 260/570.8 |
| 3,438,981 | 4/1969 | Stach | 260/240 |
| 3,781,443 | 12/1973 | Fuller et al. | 424/330 |
| 4,202,896 | 5/1980 | Gootjes | 544/397 |
| 4,314,081 | 2/1982 | Molloy et al. | 564/347 |
| 4,541,954 | 9/1985 | Borowski et al. | 260/239 |
| 4,678,775 | 7/1987 | Nathanson | 514/47 |
| 4,783,457 | 11/1988 | Nathanson | 514/227.2 |
| 4,843,071 | 6/1989 | Hohenwarter | 514/217 |
| 4,857,532 | 8/1989 | Koehler et al. | 514/262 |
| 4,866,062 | 9/1989 | Tóth et al | 514/255 |
| 4,892,871 | 1/1990 | Nathanson | 514/227.2 |
| 4,902,690 | 2/1990 | Nathanson | 514/213 |
| 4,908,365 | 3/1990 | Buzas et al. | 544/397 |
| 5,059,422 | 10/1991 | Fishbein et al. | 424/426 |

FOREIGN PATENT DOCUMENTS 3234995 3/1984 Germany.

OTHER PUBLICATIONS

Anderson, P. H., Biochemical and Pharmacological Characterization of [$^3$H]GBR 12935 Binding In Vitro to Rat Striatal Membranes: Labeling of the Dopamine Uptake Complex, *J. Neurochem.* 48: 1887-1896 (1987).

Baldessarini et al., The Uptake and Subcellular Distribution of Aromatic Amines In The Brain Of The Rat, *Journal of Neurochemistry* 18:2519-2533 (1971).

Bell et al., L(+)-2-Tropinone, *J. Am. Chem. Soc.* 82:4642-4644 (1960).

Blakely et al., Cloning and expression of a functional serotonin transporter from rat brain, *Nature* 354:66-70 (1991).

(List continued on next page.)

*Primary Examiner*—Glennon H. Hollrah
*Assistant Examiner*—John D. Pak
*Attorney, Agent, or Firm*—Sterne, Kessler, Goldstein & Fox

[57] ABSTRACT

A method of controlling an invertebrate pest, comprising contacting the pest with a pest-controlling amount of an agent having substantial inhibitory activity toward a phenylethanolamine reuptake transporter as determined by radioactive octopamine reuptake inhibition assay is disclosed. Compositions comprising compounds capable of inhibiting the octopamine reuptake transporter include chloroethylphenylamines, aryl-1,4-dialkyl piperazines, tricyclic antidepressants, and cocaine derivatives. A process for inhibiting the feeding of an invertebrate pest comprising contacting said pest with a pest-controlling amount of an agent having substantial inhibitory activity toward a phenylethanolamine reuptake transporter as determined by radioactive octopamine reuptake inhibition assay, with the proviso that said agent is not cocaine. A process for delaying the maturation of a juvenile invertebrate by contacting it with an inhibitory amount of a phenylethanolamine reuptake transporter blocker is also disclosed. A radioactive phenylethanolamine reuptake inhibition assay for determining whether a given compound is an inhibitor of octopamine neuronal transport is also disclosed.

4 Claims, 7 Drawing Sheets

OTHER PUBLICATIONS

Berger et al., [³H]GBR-12935: A Specific High Affinity Ligand For Labeling The Dopamine Transport Complex, *European Journal of Pharmacology* 107:289–290 (1985).

Bonnet et al., High-Affinity [³H]GRB 12783 Binding To A Specific Site Associated With The Neuronal Dopamine Uptake Complex In The Central Nervous System, *Eur. J. Pharm.* 126:211–222 (1986).

Bosy et al., Differential Inhibition of Synaptosomal Accumulation of [³H]–Monoamines by Cocaine, Tropacocaine and Amphetamine in Four Inbred Strains of Mice, *Pharm. Biochem. & Behav.* 34:165–172 (1989).

Breer et al., A Microscale Floatation Technique For The Isolation of Synaptosomes From Nervous Tissue of *Locusta Migratoria*, *Insect Biochem.* 10:457–463 (1980).

Carlson et al., Inactivation of Octopamine In Larval Firefly Light Organs By a High-Affinity Uptake Mechanism, *J. exp. Biol.* 122:369–385 (1986).

Carlson, A. D., Effect of Adrenergic Drugs On The Lantern Of The Larval *Photuris Firefly*, *J. Exp. Biol.* 48:381–387 (1968).

Einhorn, A., Beiträge zur Kenntniss des Cocaïns, *Chem. er.* 21:47–51 (1988).

Evans, P. D., Octopamine: A High-Affinity Uptake Mechanism In The Nervous System Of The Cockroach, *Journal of Neurochemistry* 30:1015–1022 (1978).

Fischer et al., Xylamine, an Irreversible Inhibitor of Norepinephrine Uptake, is Transported by This Same Uptake Mechanism in Cultured Rat Superior Cervical Ganglia, *J. Pharm. Exp. Ther.* 226:650–655 (1983).

Geigy, J. R., 5–(Alkylaminoalkyl)iminodibenzyls, *Chem. Abstracts* 58:11338c (1963).

Hale, J. L., Nortriptyline Hydrochloride, in *Analytical Profiles of Drug Substances*, vol. 1, Florey, K., Ed., Academic Press pp. 233–247 (1972).

Harmar et al., Octopamine-Sensitive Adenylate Cyclase in Cockroach Brain: Effects of Agonists, Antagonists, and Guanylyl Nucleotides, *Molecular Pharmacology* 13:512–520 (1977).

Hoffsommer et al., The Homoallylic Rearrangement in the Synthesis of Amitriptyline and Related Systems, *J. Org. Chem.* 27:4134–4137 (1962).

Hollingworth et al., Formamidine Pesticides: Octopamine-Like Actions in a Firefly, *Science* 208: 74–76 (1980).

Hollingworth et al., Biological and Neurotoxic Effects of Amidine Pesticides, in *Insecticide Mode of Action*, Coats, J. R., Ed., Academic Press, N.Y., pp. 189–227 (1982).

Hollingworth et al., Pharmacology And Toxicology Of Octopamine Receptors In Insects, in *IUPAC Pesticide Chemistry*, Miyamoto et al., Eds., Pergammon Press, N.Y., pp. 187–192 (1983).

Iverson, L. L., Uptake Processes For Biogenic Amines, in *Handbook of Psychopharmacology*, vol. 3, Iverson et al., Eds., Plenum Press, N.Y., pp. 381–442 (1975).

Jacob et al., Préparation de la (diméthylamino-3′ méthyl-thyl-2′propyl)-5 dihydro-10.11 dibenz-[b,-f]-azépine racémique et de ses isomerés optiques, *Compt. Rend.* 252:2117–2118 (1961).

Jaffe, J. H., Drug Addiction and Drug Abuse, *The Pharmacological Basis of Therapeutics*, Goodman, L. and Gilman A. (eds.), pp. 535–584 (1980).

Jaim-Etcheverry et al., DSP-4: A Novel Compound With Neurotoxic Effects On Noradrenergic Neurons Of Adult Developing Rats, *Brain Research* 188:513–523 (1980).

Kennedy et al., Sodium–Sensitive Cocaine Binding to Rat Striatal Membrane: Possible Relationship to Dopamine Uptake Sites, *Journal of Neurochemistry* 41:172–178 (1983).

Luo et al., Synaptosomes and Synaptosome Membrane Vesicles From The Brain of *Mamestra Configurata*: Application To Voltage-Dependent And ATP-dependent $Ca^{2+}$ Ion Trans-. . . , *Insect Biochem.* 17:911–918 (1987).

Mandras et al., Cocaine Receptors Labeled by [³H]2β-Carbomethoxy -3β-(4-fluorophenyl)tropane, *Molecular Pharmacology* 36:518–524 (1989).

Martin et al., Pyrolysis and Volatilization of Cocaine, *Journal of Analytical Toxicology* 13:158–162 (1989).

Matsumura et al., Biochemical and Physiological Effects of Chlordimeform, *Environmental Health Perspectives* 14:71–82 (1976).

Merck, W., Ueber die künstliche Darstellung von Cocain und seiner Homolgen, *Chem. Ber.* 18:2952–2955 (1885).

Nathanson et al., Octopamine-Sensitive Adenylate Cyclase: Evidence for a Biological Role of Octopamine in Nervous Tissue, *Science* 180:308–310 (1973).

(List continued on next page.)

OTHER PUBLICATIONS

Nathanson, J. A., Octopamine Receptors, Adenosine 3′, 5′-Monophosphate, and Neural Control of Firefly Flashing, *Science* 203:65–68 (1979).

Nathanson et al., N-Demethylchlordimeform: A Potent Partial Agonist of Octopamine-Sensitive Adenylate Cyclase, *Molecular Pharmacology* 20:68–75 (1981).

Nathanson, J. A., Caffeine and Related Methylxanthines: Possible Naturally Occurring Pesticides, *Science* 226:184–187 (1984).

Nathanson, J. A., Characterization of octopamine-sensitive adenylate cyclase: Elucidation of a class of potent and selective octopamine-2 receptor agonists with toxic effects . . . , *PNAS USA* 82:599–603 (1985).

Nathanson, J. A., Phenylethanolamine Receptors as Selective Targets for Pesticide Action, in *Sites of Action for Neurotoxic Pesticides*, Hollingworth and Green, eds., Am. Chem. Soc., pp. 154–161 (1987).

Nathanson, J. A., Development of a Photoaffinity Ligand for Octopamine Receptors, *Molecular Pharmacology* 35:34–43 (1989).

Nathanson et al., A Probe for Octopamine Receptors: Synthesis of 2-[(4-Azido-2,6-diethylphenyl)imino] imidazolidine and Its Tritiated Derivative, a Potent Reversible-. . . , *J. Med. Chem.* 32:1795–1799 (1989).

Nathanson, J. A., Cyclic Nucleotides and Nervous System Function, *Physiological Reviews* 57(2):157–256 (1977).

Nathanson, J. A., Cholera Toxin, Cyclic Amp, And The Firefly Flash, *Journal of Cyclic Nucleotide and Protein Phosphorlation Research* 10(2):157–166 (1985).

Nathanson, J. A., Phosphodiesterase: A Possible Site for Pesticide Action, 2nd Int'l Symp. Insect Neurobiol. Pest. Action, London, pp. 129–130, abstract (1985).

Nathanson et al., Octopamine-Sensitive Adenylate Cyclase: Properties And Pharmacological Characterization, *Neurosci. Abstr.* 5:346 (1979).

Nathanson, J. A., Octopamine-Sensitive Adenylate Cyclase And Its Possible Relationship To The Octopamine Receptor, in *Trace Amines and the Brain*, Usdin et al., Eds., Marcel Dekker, N.Y., pp. 161–190 (1976).

Nathanson, et al., Neural Control Of Light Emission In Photuris Larvae: Identification Of Octapamine-Sensitive Adenylate Cyclase, *J. Exp. Zool.* 208:255–262 (1979).

Nathanson, J. A., Phenyliminoimdazolidines, Characterization of a Class of Potent Agonists of Octapamine-Sensitive Adenylate Cyclase and Their Use in . . . , *Molec. Pharm.* 28:254–268 (1985).

Nathanson, J. A., Neurochemical Regulation of Light Emission From Photocytes, in *Insect Neurochemistry and Neurophysiology*, Borkovec, A. et al., Eds., Humana Press, N.Y., pp. 263–266 (1986).

Nathanson, J. A., Cyclic AMP Synthesis And Degradation: Possible Targets For Pesticide Action, in *Membrane Receptors and Enzymes as Targets of . . .* , Clark et al., Eds. Plenum Press, N.Y., 157–171 (1986).

Nathanson et al., Serotonin-Sensitive Adenylate Cyclase in Neural Tissue and Its Similarity to the Serotonin Receptor: A Possible Site of Action of Lysergic Acid Diethylamide, *PNAS USA* 71:797–801 (1974).

Nicholson, et al., Isolation Of Nerve Endings From The Central Nervous System Of The Cricket (*Acheta domesticus*) Using A Percoll Gradient Technique, *Insect Biochem.* 21(4):447–456 (1991).

Orchard, I., Octopamine in insects: neurotransmitter, neurohormone, and neuromodulator, *Can. J. Zool.* 60:659–669 (1982).

Pacholczyk et al., Expression Cloning of a cocaine- and antidepressant-sensitive human noradrenaline transporter, *Nature* 350:350–354 (1991).

Plowman et al., Coca Pests And Pesticides, *Journal of Ethnopharmacology* 1:263–278 (1979).

Richelson et al., Blockade By Antidepressants and Related Compounds of Biogenic Amine Uptakes Into Rat Brain Synaptosomes: Most Antidepressants Selectively Block . . . , *Eur. J. Pharm.* 104:277–286 (1984). Ritz et al., Cocaine Binding Sites Related to Drug Self-Administration, *NIDA Research Monograph* 95:239–246 (1989).

Robertson et al., Octopamine and Some Related Noncatecholic Amines In Invertebrate Nervous Systems, *Int. Rev. Neurobiol.* 19:173–224 (1976).

Schmutz et al., 29. Über in 11-Stellung amino-substituierte Dibenzo[b,f]-1,4-thiazepine und -oxazepine, *Helvetica Chimica Acta* 50:245–254 (1967).

Squibb, Hydrochlorate Of Cocaine, *The Pharmaceutical Journal And Transations*, 16:67–69 (1885).

(List continued on next page.)

OTHER PUBLICATIONS

Squibb, Hydrochlorate Of Cocaine, Or Muriate Of Cocaine, *The Pharmaceutical Journal And Transactions* 15:774–776, 796–798 (1885).

Stach et al, Beiträge zur Entwicklung psychotroper Stoffe, 2. Mitt.: Basisch substituierte Dibenzo–Oxepin–, Dibenzo–thiepin–und Dibenzo–cycloocten–Derivate, *Mh. Chem.* 93:896–904 (1962).

Whitton et al., Metabolism of tauriine by synaptosmal preparations from nsects, *Biochemical Society Transactions* 14:609–610 (1986).

Wierenga et al., Octopamine Uptake and Metabolism in the Insect Nervous System, *Journal of Neurochemistry* 54(2):479–489 (1990).

Wilhelm et al., 145. Synthese und Eigenschaften von 1–Aminoalkyl–dibenzo[b,e]bicyclo[2.2.2 octadienen, *Helv. Chim. Acta* 52:1385–1395 (1969).

Willstätter et al., Synthese des natürlichen Cocains, *Ann. der Chemie* 434:111–139 (1923).

van der Zee et al., Aryl 1,4–dialk(en)ylpiperazines as selective and very potent inhibitors of dopamine uptake, *Eur. J. Med. Chem.* 15:363–370 (1980).

International Search Report for International application No. PCT/US92/05473 (1992).

Wierenga et al., Actions of durgs and pesticides on components of octopaminergic neurotransmission, *Chemical Abstracts* 108(7) Abstract No. 51233j (1988).

INVERTEBRATE PHENYLETHANOLAMINE TRANSPORTER AND THE USE THEREOF

CROSS REFERENCE TO RELATED APPLICATIONS

The present application is a continuation-in-part of U.S. patent application Ser. No. 07/814,877, filed Jan. 2, 1992, now abandoned, which is a continuation-in-part of U.S. patent application Ser. No. 07/721,322, filed Jul. 1, 1991, the contents of which are fully incorporated herein by reference.

FIELD OF THE INVENTION

The present invention is in the field of pest-controlling agents. In particular, the invention relates to a method for inhibiting an invertebrate-specific membrane transporter protein, compounds having binding specificity therefor, and pesticidal/pestistatic compositions. This invention also relates to an in vitro assay used to determine whether a given compound is an inhibitor of octopamine neuronal transport.

BACKGROUND OF THE INVENTION

A. Octopamine and Octopamine Receptors

Octopamine (OA) was first discovered over 35 years ago in the posterior salivary gland of the octopus (V. Erspamer and G. Boretti, Arch. Int. Pharmaco. Ther. 88: 926-322 (1951)). Although similar to norepinephrine (NE) in structure, OA has very little activity as a sympathomimetic when injected into mammals (A. Lands and J. Grant, J. Pharm. Exptl. Therap. 106: 341-345 (1952)) and, compared with NE, is present in very low concentrations in vertebrate tissues (Y. Kakimoto and M;. Armstrong, J. Biol. Chem. 237: 422-427 (1962)). Relatively little attention was paid to OA until early 1970's, when Molinoff and Axelrod reported that OA was present in much higher concentrations in invertebrates, particularly in invertebrate nerve tissue (P. B. Molinoff and J. Axelrod, J. Neurochem. 19: 157-163 (1972)).

In 1973, the first identification of an OA receptor was reported (J. A. Nathanson "Cyclic AMP: A Possible Role in Insect Nervous System Function", (Ph.D. Thesis) (1973); J. A. Nathanson and P. Greengard, Science, 19: 308-310 (1973)). Because this receptor was present in highest concentrations in insect nerve cord, it was postulated that OA might function as a neurotransmitter. Furthermore, because these receptors were undetectable in mammalian tissues, it was also postulated that the neurotransmitter function of OA might be largely restricted to invertebrates (J. A. Nathanson "Cyclic AMP: A Possible Role in Insect Nervous System Function", (Ph.D. Thesis) (1973); J. A. Nathanson and P. Greengard, Science, 19: 308-310 (1973); J. A. Nathanson, Trace Amines and the Brain: Eds. Marcel Dekker, pp. 161-190 (1976)). At about the same time, Kravitz and coworkers (B. Wallace et al., Brain Res. 349-55 (1974)) independently reported the presence of OA-containing neurons in crustacea, and, somewhat later, Hoyle reported evidence suggesting the presence of large OA neurons in insect ganglia (G. Hoyle, J. Exp. Zool 193: 425-31 (1975)). Subsequent work by a number of investigators has established the role of OA, not only as a neurotransmitter, but also as a neuromodulator and circulating neurohormone in insects and acarines (for review see I. Orchard, Can. J. Zool, 60: 659-69 (1982); H. A. Robertson and A. V. Juorio, Int. Rev. Neurobiol. 19: 173-224 (1976)). Indeed, OA plays a pervasive role in regulating many areas of insect physiology, including carbohydrate metabolism, lipid mobilization, hematocyte function, heart rate, peripheral muscle tension and excitability, and behavior. The functions that OA carries out in insects appear analogous to those carried out by norepinephrine (NE) and epinephrine (EPI) in vertebrates. This has led to the suggestion that, during evolution, there may have been a divergence in the use of these amines between the two arms of the animal kingdom (H. A. Robertson and A. V. Juorio, Int. Rev. Neurobiol. 19: 173-224 (1976); A. V. Robertson and A. V. Juorio, J. Neurochem. 28: 573-79 (1977); J. A. Nathanson, Physiological Reviews 57: 158-256 (1977)).

Analogous to the action of NE and EPI in vertebrates, many of the effects of OA in invertebrates are mediated by cyclic AMP (J. A. Nathanson and P. Greengard, Science 19: 308-310 (1973); J. A. Nathanson, Physiological Reviews 57: 158-256 (1977); H. Robertson and J. Steele, J. Neurochem 19: 1603-06 (1972); A. Harmar and A. Horn, Mol. Pharmacol. 13: 512-20 (1976); C. Lingle et al., Handbook of Exptl. Pharmacology, (J. Kebabian & J. Nathanson, eds. ), pp. 787-846 (1982)). OA stimulates production of cyclic AMP through activation of OA-sensitive ($G_s$ protein-coupled) adenylate cyclase (J. A. Nathanson, J. Cyclic Nucleotide and Protein Phosphor. Res. 10: 157-66 (1985)). In 1979, it was found that the firefly light organ, in which OA mediates neural control of light emission (A. D. Carlson, Advances Insect Physiol. 6: 51-96 (1969); J. F. Case and L. G. Strause, Bioluminescence in Action (P. J. Herring, ed.), pp. 331-366 (1978)), has a virtually pure population of OA receptors present in enormous quantity, with no evidence of adenylate cyclases activated by other hormones (J. A. Nathanson, Science 203: 65-8 (1979); J. A. Nathanson and E. Hunnicutt, J. Exp. Zool. 208: 255-62 (1979a)). Thereafter, the first detailed pharmacological characterization of $G_s$-linked OA receptors was carried out in the absence of other amine receptors (J. A. Nathanson, Science 203: 65-8 (1979); J. A. Nathanson and E. Hunnicutt, J. Exp. Zool. 208: 255-62 (1979a); J. A. Nathanson, Proc. Natl. Acad. Sci. U.S.A. 82: 599-603 (1985b); Nathanson, J. A., in Insect Neurochemistry and Neurophysiology, Borkovec, A., et al., eds., Humana: Clifton, N.J., pp. 263-266 (1986); Nathanson, J. A., et al., Neurosci. Abstr. 5:346 (1979)). More recently, a new chemical class of potent OA receptor agonists has been characterized, the phenyliminoimidazolidines (PIIs) (Nathanson, J. A., Proc. Natl. Acad. Sci. U.S.A. 82: 599-603 (1985); Nathanson, J. A., Mol. Pharmacol. 28: 254-268 (1985)). With the PIIs and other compounds, it has been possible to distinguish clearly the characteristics of OA receptors from those of mammalian adrenergic, dopaminergic, and serotonergic receptors.

Overactivation of the OA system in insects and acarines leads to behavioral and physiological abnormalities that have pestistatic and pesticidal consequences. One way to cause OA overactivation, and thereby take advantage of this system for pesticide development, is to directly stimulate OA receptor proteins.

Analogous to the octopamine neurotransmitter system is the cholinergic system, where the plant alkaloid nicotine exerts natural pesticidal effects through excessive activation of acetylcholine (ACh) receptors. As is well known, for pesticide development it has turned out that, more effective than cholinergic agonists, are the reversible and irreversible acetylcholinesterase inhibitors. Acetylcholinesterase (AChE) catalyzes the hydrolysis of the neurotransmitter ACh to choline and acetate. If AChE is inhibited by a pesticide, normal inactivation of ACh is blocked, and ACh accumulates to abnormally high levels. This causes overactivation of ACh receptors, indirectly, through inhibition of neurotransmitter degradation. We have recently discovered that an analogous site of action exists for the OA system. Because of OA's selectivity for invertebrates, agents affecting this site will have reduced toxicity for vertebrates.

B. Pesticidal and Pestistatic Activity of OA Agonists in Insects and Acarinas Because OA affects so many sites in insects, it is not surprising that disruption of this system adversely affects insect physiology. In 1980, it was reported that the formamidine pesticides cause glowing of firefly light organs and it was suggested that these compounds, which have low toxicity for vertebrates, might be exerting their pesticidal actions by affecting OA receptors. Subsequently, several labs (Nathanson, J. A., et al., *Molec. Pharmacol.* 20: 68–75 (1981); Evans, P. D., et al., *Nature* 287: 60–62 (1980)), determined that the formamidines are indeed potent OA agonists in several insect species. In addition, it was found that OA itself, as well as OA analogs and the PIIs applied to leaves, could markedly interfere with the feeding of *M. sexta* (Nathanson, J. A., *Proc. Natl. Acad. Sci. U.S.A.* 82: 599–603 (1985); Nathanson, J. A., in *Insect Neurochemistry and Neurophysiology*, Borkovec, A., et al., eds., Humana: Clifton. N.J., pp. 263–266 (1986); Nathanson, J. A., *Mol. Pharmacol.* 28: 254–268 (1985); Nathanson, J. A., in *Sites of Action for Neurotoxic Pesticides*, Hollingworth. R., et al., eds., Am. Chem. Soc.: Washington, D.C., pp. 154–161 (1987): Nathanson, J. A., *Science* 226: 184–187 (1984); Nathanson, J. A., in *Abstr. 2nd Internatl. Symp. Insect Neurobiol. Pest. Action*, Society of Chemical Industry: London, pp. 129–130 (1985); Nathanson, J. A., in *Membrane Receptors and Enzyme as Targets of Insecticidal Action*, Clark, J., et al., Plenum: New York, pp. 157–171 (1986)). The behavioral and pestistatic effects of these compounds on Manduca were similar to those of the formamidines: they caused tremors, hyperactivity, rearing, and poor coordination (resulting in leaf drop-off), abnormalities which, interestingly, are reminiscent of the effects of overdoses of amphetamines and adrenergic agonists in vertebrates.

Additional support for a connection between overactivation of the OA system and pesticidal activity has come from observations showing that the known species variation in the pesticidal effects of formamidines (Matsumura, F., et al., *Environ. Health Perspect.* 14: 71–82 (1976)) is related to the ability of these compounds to activate $G_s$-coupled OA receptors ($G_s$-coupled receptors are those whose activation results in the stimulation of adenylate cyclase and the synthesis of cyclic AMP). For example, in Manduca, a sensitive species, we have found (Nathanson, J. A., *Mol. Pharmacol.* 28: 254–268 (1985)) that didemethylchlordimeform (DDCDM) is a full OA agonist, 20-fold more potent than OA, while in cockroach, a resistant species, DDCDM is much weaker than OA in activating adenylate cyclase. This species variability appears to result from the distribution of OA receptor subtypes that need to be specifically targeted for pesticide activity. (Additional evidence for involvement of $G_s$ (cAMP-linked) OA receptors comes from the observations (Nathanson, J. A., *Proc. Natl. Acad. Sci. U.S.A.* 82: 599–603 (1985) that the antifeeding effects of OA agonists are enhanced by inhibitors of cAMP catabolism and mimicked by adenylate cyclase activators (forskolin) and lipid-soluble cAMP analogs.)

C. Cocaine and the Amine Reuptake Site

Although cocaine has a fascinating medicinal history in man, dating back at least 4500 years, its natural function in plants is unknown (Plowman, T., in *Ethnobotany in the Neotropics*, Prance, G. T., et al., eds., N.Y. Botanical Garden, Bronx, N.Y., pp. 62–111 (1984)). Plowman, Rivier and others (Rivier, L., *J. Ethnopharmacology* 3: 313–335 ( 1981 ); Plowman, T., et al., *Ann. Bot.* (London) 51: 641–659 (1983)) have determined that the four major varieties of Erythroxylum (coca) plants that produce cocaine, contain levels ranging from 0.35–0.72% dry weight, with values often exceeding 1% (particularly in small, newly emerging leaves). Although relatively little is known about the insect pests of coca, Plowman & Well (*J. Ethnopharmacology* 1: 263–278 (1979)) have commented, on the basis of personal observations, that:

> Compared with other tropical American crops, *E. coca* and *E. novogranatense* are relatively pest-free. Herbivorous insects are only rarely observed on the plants in the field; damage to leaves is often minor. This is especially noteworthy since, during much of the year, the membranaceous leaves of coca are found in the tender state of unfolding, the result of their being stripped 3–6 times a year during harvest.

D. Amine Reuptake in The Adrenergic System

In sympathetic neuroeffector junctions, termination of norepinephrine (NE) action is effected by active reuptake into the nerve by a membrane-bound amine reuptake transport system. This process is largely responsible for the termination of the effects of adrenergic impulses in most organs. To effect the reuptake of norepinephrine into adrenergic nerve terminals and to maintain the concentration gradient of norepinephrine within the vesicles, at least two distinct carrier-mediated transport systems are involved: one across the axoplasmic membrane from the extracellular fluid to the cytoplasm; and the other from the cytoplasm into the storage vesicles.

Due to the relative ease of isolating pure preparations of granules, especially from the adrenal medulla, the transport system of the storage granule has been well-characterized. It can concentrate catecholamines against a 200-fold gradient across the membrane of the chromaffin granule. This transport system requires ATP and $Mg^{2+}$, and it is blocked by low concentrations (40 nM) of reserpine. Uptake of catecholamine and ATP into isolated chromaffin granules appears to be driven by pH and potential gradients that are established by an ATP-dependent proton translocase (Winkler et al., Molecular organization of vesicles storing transmitter: chromaffin vesicles as a model. In, *Chemical Neurotransmission*—75 years, (Stjärne et al., eds.) Academic Press, Ltd., London, 1981, pp. 57–68).

The amine transport system across the axoplasmic membrane is $Na^+$ dependent and is blocked by a number of drugs, including cocaine and the tricyclic antidepressants, such as imipramine. This transporter has a high affinity for norepinephrine and a somewhat lower affinity for epinephrine; the synthetic $\beta$-adrenergic agonist isoproterenol is not a substrate for this system. The neuronal uptake process has been termed uptake-1 (Iversen, L. L., Uptake processes for biogenic amines. In, *Handbook of Psychopharmacology*, Vol. 3 (Iversen et al., eds.) Plenum Press, New York, pp. 381–442, 1975). There is also an extraneuronal amine transport system, termed uptake-2, which exhibits a low affinity for norepinephrine, a somewhat higher affinity for epinephrine, and a still higher affinity for isoproterenol. This uptake process is quite ubiquitous and is present in glial, hepatic, myocardial, and other cells. Uptake-2 is not inhibited by imipramine or cocaine. It is probably of relatively little physiological importance unless the neuronal uptake mechanism is blocked (Iversen, 1975, Id.; Trendelenburg, U., A kinetic analysis of the extraneuronal uptake and metabolism of catecholamines, *Rev. Physiol. Biochem. Pharmacol.*, 87: 33–115 (1980)). It may be of greater importance in the disposition of circulating catecholamines than in the removal of amines that have been released from adrenergic nerve terminals.

In mammals, the CNS stimulatory and euphoric effects of cocaine are thought to be due to cocaine's well-documented action in blocking dopamine (DA) reuptake into presynaptic nerve terminals (Jaffe, J., in *The Pharmacological Basis of Therapeutics*, Gilman, A. G., et al., eds., MacMillan: New York, pp. 535–584 (1980); Kennedy, L., et al., *J. Neurochem.* 41: 172–178 (1983)). Because amine reuptake is a major mechanism for inactivation of DA following its synaptic release, the effect of cocaine is to augment and prolong DA neurotransmission. In man, with moderate amounts of cocaine, this results in mild verbal and motor activation which is reinforcing but in excess cocaine may cause hyperactivity, tremors, incoordination, vomiting, and tonic-clonic convulsions.

Pharmacological evidence from vertebrates supports the presence of distinct reuptake sites (amine transporter proteins) for DA, NE, and serotonin (5-HT) (Ritz, M., et al., NIDA Research Monograph 95: 239–246 (1989)). Although much recent emphasis has been put on cocaine's action on DA, older literature clearly indicates that cocaine also blocks the reuptake of NE and 5-HT (Baldessarini, R., et al., *J. Neurochem.* 18: 2519–2533 (1971); Body, T., et al., *Pharmacol. Biochem. & Behavior* 34: 165–172 (1989)).

Early biochemical studies of monoamine reuptake in mammals involved the use of living animals injected with labeled amines or the use of intact, isolated organs or tissue fragments incubated in vitro with tracer (Hertting et al., *J. Pharmacol. Exp. Ther.* 134: 146–153 (1961); Dengler et al., *Nature* 191: 816–817 (1961); Axelrod and Inscoe, *J. Pharmacol. Exp. Ther.* 141: 161–165 (1963)). Although these studies yielded important data about reuptake kinetics, they have been less useful for pharmacologically characterizing transporter binding sites and for determining the structure-activity relationships of drugs capable of blocking these sites. This is due to the fact that drug penetration through intact tissues and drug metabolism within tissues can significantly alter measurement of the true affinity of compounds for transporter binding sites. Studies with intact tissue are also tedious and complicate the use of replicate samples because of the tube-to-tube variability in the size and homogeneity of the intact tissue pieces. Thus, many researchers have abandoned the use of intact tissue preparations in the characterization of vertebrate amine transporters and have used, instead, broken cell tissue fractions prepared in such a way as to contain intact pinched-off nerve endings (synaptosomes) capable of accumulating labeled amines under sodium- and energy-dependent conditions (Baldessarini and Vogt, *J. Neurochem* 18: 2519–2533 (1971); Anderson, *J. Neurochem* 48: 1887–1896 (1987); Boja and Kuhar, *Europ. J. Pharmacol.* 173: 215–217 (1989).

In insects, uptake studies of monoamines have been largely limited to the study of octopamine, where evidence from intact tissue experiments supports the presence of a high affinity sodium-dependent transporter (Evans, *J. Neurochem* 30: 1015–1022 (1978); Carlson and Evans, *J. Exp. Biol.* 122: 369–385 (1986); Wierenga and Hollingworth, *J. Neurochem.* 54: 479–489 (1990)). These studies have utilized either intact ventral nerve cord or intact pieces of tissue incubated in insect saline. Surprisingly, there appears to be no report of the examination of the uptake of octopamine or other monoamines in synaptosomal-containing broken cell fractions. This appears to be the case despite the fact that several reports have described preparations of both crude and purified synaptosomal fractions (Breer and Jererich, *Insect Biochem.* 10: 457–463 (1980); Whitton et al., *Biochem. Soc. Trans.* 14: 609–610 (1986); Luo and Bodnaryk, *Insect Biochem.* 17: 911–918 (1987); Nicholson and Connelly, *Insect Biochem.* 21: 447–456 (1991)).

SUMMARY OF THE INVENTION

Octopamine (OA) is an invertebrate-specific neurotransmitter. The question of whether there might be some way to create a more general overactivation of the OA system, coupled with our curiosity about the role of cocaine in plants, has led us to discover a new site for pesticide action. It has been discovered that when the invertebrate octopamine reuptake transporter is blocked by several classes of compounds, herein described, the result is pest-controlling activity. Antifeeding experiments show that cocaine is a strong deterrent to leaf feeding by the blocking of the OA reuptake transporter, thus causing a general overstimulation of the octopaminergic system that has pestistatic and pesticidal effects. Moreover, it has also been discovered that the combination of a reuptake inhibitor with a phenylethanolamine such as OA has a synergistic effect on invertebrate pests.

The invention is directed to a method of controlling an invertebrate pest, comprising contacting the pest with a pest-controlling amount of an agent having substantial inhibitory activity toward a phenylethanolamine reuptake transporter, as determined by radioactive octopamine reuptake inhibition assay. Reuptake is substantially inhibited when the agent is present at a concentration of from about $10^{-12}$ molar (M) to about $10^{-3}$M, or from about $10^{-12}$M to about $10^{-2}$M, and reuptake of a phenylethanolamine, e.g., octopamine, is inhibited from about 25 to about 100 percent as compared to reuptake by a control.

The invention is directed to a method of controlling an invertebrate pest wherein the agent is a chloroethylphenylamine and has the formula

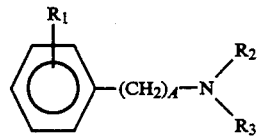

wherein:

$R_1$ is a halogen or $C_1-C_6$ alkyl;
$R_2$ is a chlorinated $C_1-C_6$ alkyl;
$R_3$ is a $C_1-C_6$ alkyl; and
A is 1–6.

The invention is directed to a method of controlling an invertebrate pest wherein the agent is an aryl-1,4-dialk(en)yl piperazine and has the formula

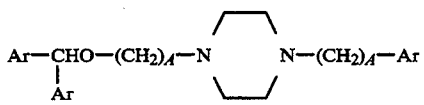

wherein:
Ar is independently aryl or heteroaryl wherein aryl or heteroaryl can be substituted by hydrogen, halogen such as chloro, fluoro, bromo, iodo, $CF_3$, $C_1-C_6$ alkoxy, $C_2-C_6$ dialkoxymethyl, $C_1-C_6$ alkyl, cyano, $C_3-C_{15}$ dialkylaminoalkyl, carboxy, carboxamido, $C_1-C_6$ haloalkyl, $C_1-C_6$ haloalkylthio, allyl, aralkyl, $C_3-C_6$ cycloalkyl, aroyl, aralkoxy, $C_2-C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3-C_6$ heterocycloalkyl, a $C_3-C_6$ heterocycloalkyl ring fused to a benzene ring, $C_1-C_6$ alkylthio, $C_1-C_6$ alkylsulfonyl, $C_1-C6$ haloalkylsulfonyl, $C_1-C_6$ alkylsulfinyl, $C_1-C_6$ haloalkylsulfinyl, arylthio, $C_1-C_6$ haloalkoxy, amino, $C_1-C_6$ alkylamino, $C_2-C_{15}$ dialkylamino, hydroxy, carbamoyl, $C_1-C_6$ N-alkylcarbamoyl, $C_2-C_{15}$ N,N-dialkylcarbamoyl, nitro and $C_2-C_{15}$ dialkylsulfamoyl; and
A is independently 1 to 6.

The invention is also directed to a method of controlling an invertebrate pest wherein said agent is a cocaine derivative and has the formula

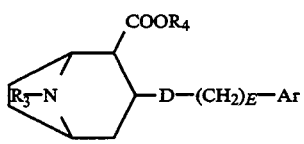

wherein Ar is independently aryl or heteroaryl wherein aryl or heteroaryl can be substituted by hydrogen, halogen such as chloro, fluoro, bromo, iodo, $CF_3$, $C_1-C_6$ alkoxy, $C_2-C_6$ dialkoxymethyl, $C_1-C_6$ alkyl, cyano, $C_3-C_{15}$ dialkylaminoalkyl, carboxy, carboxamido, $C_1-C_6$ haloalkyl, $C_1-C_6$ haloalkylthio, allyl, aralkyl, $C_3-C_6$ cycloalkyl, aroyl, aralkoxy, $C_2-C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3-C_6$ heterocycloalkyl, a $C_3-C_6$ heterocycloalkyl ring fused to a benzene ring, $C_1-C_6$ alkylthio, $C_1-C_6$ alkylsulfonyl, $C_1-C_6$ haloalkylsulfonyl, $C_1-C_6$ alkylsulfinyl, $C_1-C_6$ haloalkylsulfinyl, arylthio, $C_1-C_6$ haloalkoxy, amino, $C_1-C_6$ alkylamino, $C_2-C_{15}$ dialkylamino, hydroxy, carbamoyl, $C_1-C_6$ N-alkylcarbamoyl, $C_2-C_{15}$ N,N-dialkylcarbamoyl, nitro and $C_2-C_{15}$ dialkylsulfamoyl;

$R_3$ and $R_4$ are independently a $C_1-C_6$ alkyl;

D can be oxygen, nitrogen, sulfur, carbonyl, carboxyl, amido, $C_1-C_6$-N-alkyl amido, or dithio carboxyl; and
E is from 0 to 6.

The invention is also directed to a method of controlling an invertebrate pest with a compound selected from the class of tricyclic antidepressants.

The invention is also directed to a pest-controlling compound which comprises an agent having substantial inhibitory activity toward a phenylethanolamine reuptake transporter as determined by radioactive octopamine reuptake inhibition assay. Reuptake is substantially inhibited when the agent is present at a concentration of from about $10^{-12}M$ to about $10^{-3}M$, or from about $10^{-12}M$ to about $10^{-2}M$, and inhibition of reuptake of a phenylethanolamine, e.g., octopamine, is from about 25 to about 100 percent as compared to reuptake by the control.

The invention is also directed to a pesticidal composition comprising a reuptake inhibiting agent in the form of a powder, a water dispersion, an emulsion, or a dispersion, formulated together with a pesticidally inert carrier.

The invention is also directed to a synergistic pest-controlling composition which comprises: a pest-controlling amount of an agent having substantial inhibitory activity toward a phenylethanolamine reuptake transporter as determined by radioactive reuptake inhibition assay; and a pest-controlling amount of a phenylethanolamine or other agonists of octopamine receptors. The phenylethanolamine may be octopamine.

The invention is also directed to a process for inhibiting the feeding of an invertebrate pest comprising conducting said pest with a pest-controlling amount an agent having substantial inhibitory activity toward a phenylethanolamine reuptake transporter as determined by radioactive octopamine reuptake inhibition assay, with the proviso that said agent is not cocaine.

The invention is also directed to a process for delaying the maturation of a juvenile invertebrate by contacting it with a pest-controlling amount of an agent having substantial inhibitory activity toward a phenylethanolamine reuptake transporter as determined by radioactive octopamine reuptake inhibition assay, with the proviso that said agent is not cocaine.

The invention is also directed to a radioactive octopamine reuptake inhibition assay for determining whether a given compound is an inhibitor of octopamine neuronal transport. This in vitro assay measures the uptake of radioactive phenylethanolamine into membrane (broken cell) preparations, or more preferably, into intact tissue or synaptosomal preparations, derived from insect or other invertebrate nerve tissue.

The phenylethanolamine reuptake inhibitors of the invention are highly selective pest control agents since vertebrate species-as opposed to invertebrate, e.g., insect, species-lack phenylethanolamine reuptake transporters selective for octopamine. In addition, these phenylethanolamine reuptake inhibitors unexpectedly have synergistic activity when combined with other phenylethanolamine octopamine agonists, particularly the phenylethanolamine octopamine, as an antifeeding composition.

BRIEF DESCRIPTION OF THE DRAWINGS

FIG. 9 shows that cyproheptadine alone inhibited feeding of M. sexta and potentiated the antifeeding effects of OA.

FIG. 10 shows that injection of OA alone into isolated firefly tails results in a dose-dependent increase in light emission. Simultaneous injection of a fixed dose of cocaine potentiates this action of OA, causing a leftward shift in the OA dose-response curve by a factor of about 10. The Firefly Lantern Assay is described in the specification under "In vivo Methods."

DETAILED DESCRIPTION OF THE INVENTION

The present invention relates to the discovery of the pesticidal potential of an invertebrate-specific membrane transporter and compounds for the inhibition of the transporter. In particular, the invention relates to the phenylethanolamine reuptake transporter protein and compounds having binding specificity for it, and pesticidal/pestistatic compositions thereof.

Figure 1:
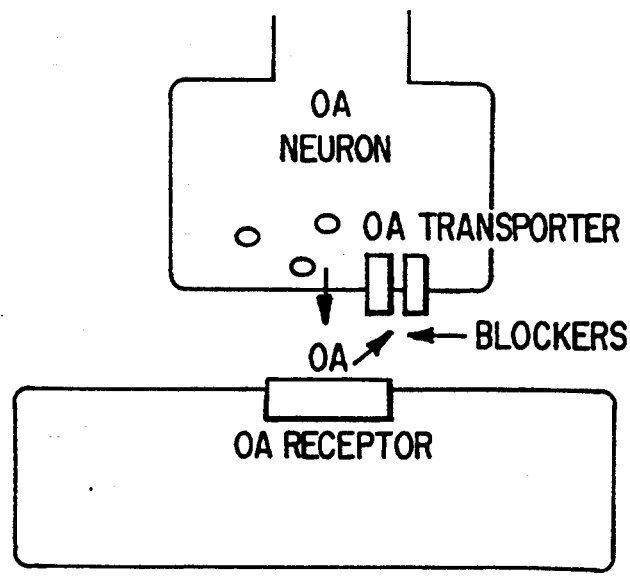
FIG. 1 is a hypothetical schematic depiction of the components involved in octopaminergic neurotransmission in invertebrates. The OA-containing neuron is shown containing OA-containing vesicles (black circles). The post-synaptic membrane is shown with an OA receptor. Release of OA into the synaptic gap allows binding of OA to the OA receptor. The pre-synaptic membrane is depicted containing OA reuptake transporter proteins. It is theorized that OA transporter blockers block the reuptake of octopamine into the pre-synaptic membrane, thereby causing increased binding of OA to susceptible OA receptors.

FIG. 1 is a hypothetical schematic depiction of the components involved in octopaminergic neurotransmission in invertebrates. The OA-containing neuron is shown containing OA-containing vesicles (black circles). The post-synaptic membrane is shown with an OA receptor. Release of OA into the synaptic gap allows binding of OA to the OA receptor. The pre-synaptic membrane is depicted containing OA reuptake transporter proteins. It is theorized that OA transporter blockers block the reuptake of octopamine into the pre-synaptic membrane, thereby causing increased binding of OA to susceptible OA receptors.

By the term "phenylethanolamine reuptake inhibitor" is intended compounds which block the reuptake of a phenylethanolamine compound by a phenylethanolamine reuptake protein. A first class of such inhibitors is the chloroethylamines, represented by the formula

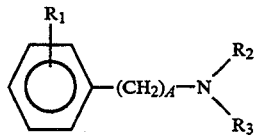

wherein:
$R_1$ is a halogen or $C_1$-$C_6$ alkyl;
$R_2$ is a chlorinated $C_1$-$C_6$ alkyl;
$R_3$ is a $C_1$-$C_6$ alkyl; and
A is 1-6.

Synthesis of two representative chloroethylamines, xylamine and DSP-4, are reported in Fisher et al., *J. Pharmacol Exp. Ther.* 226:650 (1983); and for DSP-4 Etcheverry et al., *Brain Res.* 188:513 (1980).

A second class of phenylethanolamine reuptake inhibitors is the aryl-1,4-dialk(en)yl piperazines which have the formula

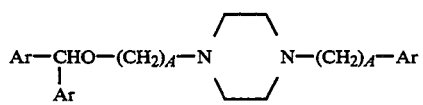

wherein:
Ar is independently aryl or heteroaryl wherein aryl or heteroaryl can be substituted by hydrogen, halogen such as chloro, fluoro, bromo, iodo, $CF_3$, $C_1$-$C_6$ alkoxy, $C_2$-$C_6$ dialkoxymethyl, $C_1$-$C_6$ alkyl, cyano, $C_3$-$C_{15}$ dialkylaminoalkyl, carboxy, carboxamido, $C_1$-$C_6$ haloalkyl, $C_1$-$C_6$ haloalkylthio, allyl, aralkyl, $C_3$-$C_6$ cycloalkyl, aroyl, aralkoxy, $C_2$-$C_6$ acyl, aryl, substituted aryl, heteroaryl, substituted heteroaryl, an aryl ring fused to a substituted benzene ring, a substituted aryl ring fused to a benzene ring, a heteroaryl ring fused to a benzene ring, a substituted heteroaryl ring fused to a benzene ring, $C_3$-$C_6$ heterocycloalkyl, a $C_3$-$C_6$ heterocycloalkyl ring fused to a benzene ring, $C_1$-$C_6$ alkylthio, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, arylthio, $C_1$-$C_6$ haloalkoxy, amino, $C_1$-$C_6$ alkylamino, $C_2$-$C_{15}$ dialkylamino, hydroxy, carbamoyl, $C_1$-$C_6$ N-alkylcarbamoyl, $C_2$-$C_{15}$ N,N-dialkylcarbamoyl, nitro and $C_2$-$C_{15}$ dialkylsulfamoyl; and A is 1-6.

By "aryl" is meant substituents such as phenyl, naphthyl, acenaphthyl, phenanthryl, etc.

By "heteroaryl" is meant substituents such as thienyl, benzo[b]thienyl, pyrrolyl, imidazolyl, pyridyl, pyrazinyl, pyrimidinyl, 3H-indolyl, furyl, chromenyl, etc.

By "$C_1$-$C_6$ alkyl" is meant substituents such as methyl, ethyl, propyl, isopropyl, butyl, isobutyl, t-butyl, pentyl, isopentyl, t-pentyl, hexyl, isohexyl, t-hexyl.

By "halogen" is meant substituents such as fluoro, chloro, bromo, and iodo.

Synthesis of GBR 12909 and many other related compounds is reported by Van der Zee, et al., *Eur. J. Med. Chem.* 15: 363-370 (1980).

A third class of phenylethanolamine reuptake inhibitors is the alkaloid cocaine and related derivatives which have the formula

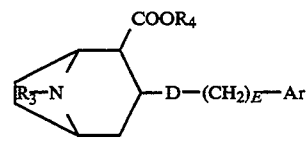

wherein Ar, $R_3$ is as defined above;
$R_4$ is a $C_1$-$C_6$ alkyl;
D can be oxygen, nitrogen, sulfur, carbonyl, carboxyl, amido, $C_1$-$C_6$-N-alkyl amido, or dithio carboxyl; and
E is 0 to 6.

Cocaine is a natural alkaloid derived from the leaves of the Erythroxylon species of coca plants. The extraction procedure is reported in Squibb, *Pharm. J.* 15[3]:775, 796; Squibb, *Pharm. J.* 6: 67-69 (1885). Synthesis of cocaine is reported in Willst ätter et al., *Ann. der Chemie* 434: 111-139 (1923). Derivatives of cocaine include, but are not limited to, cocaethylene (ecgonine ethyl ester benzoate), ecgonine hydrochloride ((-)-β-hydroxy-1-α-H,5-α-H-tropane-2-β-carboxylic acid hydrochloride) and ecgonidine methyl ester mesylate ((1R)-8-methyl-8-azabicyclo[3,2,1]oct-2-ene2-carboxylic acid methyl ester mesylate). Synthesis of cocaethylene is reported in Merck, *Ber.* 18, 2952 (1885); Einhorn, ibid. 21, 47 (1888). Synthesis of ecgonine hydrochloride may be obtained via the hydrolysis of cocaine (Wills ätter et al., *Ann. der Chemie.* 434: 111-139 (1923); Bell, Archer, *J. Am. Chem. Soc.* 82: 4642-44 (1960)). The production of methylecgonine resulting from the pyrolysis and volatilization of cocaine is reported by Martin et al., *J. Ana. Toxicol.* 13(3): 158-162 (1989).

The fourth class of phenylethanolamine re-uptake inhibitors include, but are not limited to, the tricyclic antidepressants exemplified by desipramine, imipramine, amoxapine, nortriptyline, protriptyline, maprotiline, doxepin, and pharmaceutically acceptable salts thereof. Methods of preparation of desipramine hydrochloride are described in Belgian Patent No. 614,616 (C.A. 58:11338C (1963)). Preparation of the free base anhydrochloride is disclosed in British Patent No. 908,788 (1962). The preparation of amoxapine, a known anti-depressant, is reported by Schmultz, J., et al., *Helv. Chim. Acta* 15:245 (1967). The preparation of nortriptyline, another known anti-depressant, is reported by Hoffsommer et al., *J. Org. Chem.* 27: 4134-37 (1962). A comprehensive description of nortriptyline is provided by Hale, J. L., in *Analytical Profiles of Drug Substances*, Vol. 1, K. Florey, Ed. (Academic Press, New York, 1972), pp. 233-247. The synthesis of the anti-depressant protriptyline is described in U.S. Pat. Nos. 3,244,748 and 3,271,451, and in Belgian Patent No. 617,967. Preparation of the anti-depressant maprotiline is reported in Swiss Patent Nos. 467,237 and 467,747, and in Wilhelm et al., *Helv. Chim. Acta* 52: 1385-95 (1969). Preparation of imipramine hydrochloride is reported in U.S. Pat. No. 2,554,736 and in Remington's *Pharmaceutical Sciences*, Osol, R., Ed., Mack Publishing Co., Easton, Pa., p. 1040 (1980). The preparation of doxepin is reported in Stach et al., *Monatsc.* 93: 896-904 (1962), and Bickelhaupt et al., ibid. 95:485 (1964), and in U.S. Pat. No. 3,438,981 (1969). The preparation of trimipramine is reported by Jacob Messer, *Compt. Rend.* 252:2117 (1961).

The preparation of the atypical antidepressant fluoxetine, which also has demonstrated activity as a phenylethanolamine reuptake transporter inhibitor, is reported by Malloy, B. B., Schmiegel, K. K., German Patent No. 2,500,110; Eidem, U.S. Pat. No. 4,314,081.

The terms "pest controlling amount" or "controlling an invertebrate pest," used throughout the specification and claims, are meant to include any pesticidal (killing) or pestistatic (preventing the host plant from being eaten, or inhibiting, maiming or generally interfering) activities of a composition against a given pest at any stage in its life cycle. Thus, these terms not only include killing, but also include the production of behavioral abnormalities (e.g., tremor, incoordination, hyperactivity, anorexia, leaf walk-off behavior) which interfere with activities such as, but not limited to, eating, molting, hatching, mobility or plant attachment. The terms also include chemosterilant activity which produces sterility in insects by preventing the production of ova or sperm, by causing death of sperm or ova, or by producing severe injury to the genetic material of sperm or ova, so that the larvae that are produced do not develop into mature progeny.

The terms also include repellant activity that protect animals, plants or products from insect attack by making food or living conditions unattractive or offensive. These repellant activities may be the result of repellents which may be poisonous, mildly toxic, or non-poisonous.

The term "substantial inhibitory activity" describes agents identified through the radioactive octopamine reuptake inhibition assay, described below. Essentially any chemical agent, present at a concentration of from about $10^{-12}$ molar (M) to about $10^{-3}$M, or from about $10^{-12}$M to about $10^{-2}$M, and demonstrating inhibition of from about 25 to about 100 percent as compared to the control, is considered a pest-controlling agent having a substantial inhibitory activity.

The term "radioactive octopamine reuptake inhibition assay" is meant to indicate the assay described herein more fully below. This assay is used to determine whether a given compound has any phenylethanolamine reuptake transporter-inhibiting activity. A compound that comes within this definition is one that decreases the uptake of radioactive octopamine when, over a range of concentrations from about $10^{-12}$ to about $10^{-3}$ moles per liter (M), or from about $10^{-12}$M to about $10^{-2}$M, there is a decrease of uptake from about 25 to about 100 per cent, relative to the control.

In particular, the invention relates to an in vitro method for determining whether a given compound is an inhibitor of octopamine neuronal transport. The assay is performed by contacting a neuronal invertebrate tissue sample with radiolabelled phenylethanolamine and the test compound, which may be present over a range of concentrations from about $10^{-12}$M to about $10^{-3}$M, or from about $10^{-12}$M to about $10^{-2}$M. After terminating contact with the radiolabelled phenylethanolamine, the tissue sample is then washed to remove unbound radiolabelled phenylethanolamine. The amount of radiolabelled phenylethanolamine bound or taken up by the tissue is then detected and compared with the amount of the label bound or taken up by tissue which had been contacted with radiolabelled phenylethanolamine in the absence of the compound. A relative decrease in the amount of label bound or taken up by the tissue in the presence of the compound indicates that the inhibition of octopamine neuronal transport has occurred. Preferably, the extent of decrease is at least about 25%.

The in vitro assay measures the uptake of radioactive phenylethanolamine into a tissue sample from an invertebrate pest. Preferably, the assay uses either intact tissue or a synaptosomal preparation from an invertebrate pest. The preferred invertebrate pests include, but are not limited to, *Periplaneta americana*, Blaberus, and *Manduca sexta*.

To measure uptake into intact tissue, nerve tissue is obtained from an invertebrate pest. The preferred nerve tissue is hemisected cerebral ganglia and thoracic ganglia. The isolated nerve tissue is pre-incubated at 24°-32° C. (preferably, 28° C.) for about 15 minutes in any saline solution compatible with neuronal invertebrate tissue. The preferred saline solution is a modified insect saline solution containing, e.g. 10 mM D-glucose; 130 mM NaCl; 8 mM KCl; 2 mM CaCl$_2$; 2 mM MgCl$_2$; 2.5 mM K$_2$CO$_3$; 2 mg/ml ascorbic acid; and 50 mM HEPES buffer. In the preferred insect saline solution, the pH is adjusted with NaOH to about pH 7.2 (at 31° C.), which gives a final sodium concentration of about 155-160 mM and an osmolality of about 350-355. To measure sodium-dependent uptake, some ganglia are pre-incubated in a sodium-free saline solution in which sodium chloride is omitted and an equiosmolar amount of Tris buffer (17.6 g Tris HCl and 4.54 g Tris base per liter) added ("sodium-free saline solution"). Both sodium-containing and sodium-free saline solutions may also contain 1 μM pargyline HCl.

After preincubation, uptake is measured in any suitable container, preferably, a multi-well tissue culture dish. In the preferred container, the tissue is placed in wells which contain just enough saline solution to barely cover the tissue pieces, thereby facilitating oxygenation under room atmospheric conditions. Some wells contain the compound to be assayed while others contain sodium-free saline solution. Radiolabelled octopamine or other phenylethanolamine described herein is present in all wells, preferably, at a final concentration of approximately 1 μM and 5 μCi/ml.

Following incubation for about 15 min at 24°-32° C. (preferably, 28° C.), tissue pieces are transferred to ice-cold saline solution (or sodium-free saline solution), gently agitated (preferably, for 30 sec), then transferred to a second ice-cold wash (preferably, for 30 sec), prior to final transfer to scintillation vials, where tissue is dissolved overnight, preferably, by incubating the tissue in 0.5 ml of 0.5N NaOH. After the tissue has dissolved, radioactivity is quantitated and sodium-dependent uptake is calculated on the basis of pmol amine/mg protein.

To measure uptake into synaptosomal preparations, the ganglia from the invertebrate pest of interest is rinsed briefly in a cold sucrose solution, preferably, 0.32M sucrose containing 15 mM Tris maleate pH 7.2.

(A higher sucrose concentration (0.5–0.8M) may improve synaptosomal yield in some species.) The ganglia is then transferred in a sucrose solution, preferably, in 1 ml of sucrose/Tris (usually 50 mg tissue/ml) to a homogenizer. Preferably, the homogenizer is a 2 ml-sized Teflon-glass homogenizer with 0.25 mm clearance. Tissue is then gently homogenized on ice, preferably, at 200 rpm with 10 up and down strokes. The homogenate is transferred to a 12 ml conical plastic tissue-culture tube, 9 ml of cold sucrose solution added, and the mixture centrifuged, preferably, at $800 \times g$ for 10 min in the cold in a swinging bucket rotor.

After discarding the pellet, the supernatant is transferred to a tube and recentrifuged, preferably at $40,000 \times g$ for 30 min, in a fixed angle rotor. The resulting pellet: is resuspended by gentle trituration in the sucrose solution, preferably at 50 mg original wet weight/ml, transferred to the original homogenizer, and gently rehomogenized, by hand, to a uniform suspension. This synaptosomal fraction (a 10X stock concentration for most studies) is then stored on ice until use in uptake studies.

Uptake may be measured in any suitable container, preferably, $14 \times 89$ mm clear, thin-walled, high speed plastic centrifugation tubes. An aliquot (preferably, 140 µl) of saline solution or sodium-free saline solution (described above) is added to each tube. Ascorbic acid (2 mg/ml) may be present to reduce oxidation of amines. Pargyline (1 µM) may also be added to inhibit monoamine oxidase (MAO), although, in insects, it is unclear whether or not MAO plays a major role in enzymatic degradation of monoamines.

Tubes are cooled (preferably, to about 4° C.), and radiolabelled octopamine or other phenylethanolamine is added. As described herein, there are many forms of radiolabel which are suitable for the assay. The preferred radiolabel is tritium and the preferred specific activity is 10–40 Ci/mmol, with a final concentration of tritiated octopamine or other phenylethanolamine at 0.5–5 µM in a volume of 20 µl. After adding the drugs (preferably, in a volume of 20 µl of water), tubes are preincubated at about 31° C. for about 5 min.

The uptake incubation (approximately 10 min at about 31° C.) is started by the addition of 10X synaptosomal fraction (preferably, 20 µl) in sucrose solution. Uptake incubation is terminated by pipetting the contents of the incubation tubes to new tubes half-filled with ice-cold incubation saline solution (or sodium-free saline solution), preferably containing 1 mM phentolamine mesylate and 75 µl of tissue carrier fraction. An equal volume of ice-cold incubation saline solution (or sodium-free saline solution) with phentolamine is added and tubes are centrifuged, preferably for 20 min at $40,000 \times g$, and the supernatant carefully aspirated under low vacuum with a pasteur pipette.

The pellet is left undisturbed, but rapidly and gently washed with about 4 ml of the appropriate ice-cold buffer for approximately 30 sec. Buffer is carefully aspirated and the intact pellet washed gently again with ice-cold buffer for about 30 sec. Following aspiration of the wash, any remaining droplets on the tube nails or bottom are meticulously aspirated, then 0.8 ml of 0.3N NaOH is added directly to the bottom of the tube, and the tube left undisturbed (not vortexed) for several hours to dissolve the pellet. The pellet is then gently triturated (not vortexed) and transferred to a scintillation vial for counting of uptake.

The term "tissue carrier fraction," noted above, is meant to indicate a homogenate of neuronal tissue which is used to increase the recovery of synaptosomes during sedimentation. Surprisingly, the use of the tissue carrier fraction results in a greater than 10-fold increase in recoverable sodium-dependent amine uptake. Preferably, the tissue carrier fraction is a hypotonically-lysed homogenate of rat brain tissue. More preferably, the tissue carrier fraction is prepared by thawing frozen rat brains on ice, removing the brainstem and cerebellum, and thoroughly homogenizing the cerebrum in distilled water (1 brain/10 ml) in a glass/glass homogenizer. The homogenate is centrifuged, preferably, at $40,000 \times g$ for 20 min, the supernatant discarded, and the pellet resuspended in 10 ml of distilled water and again centrifuged. The final pellet is resuspended by homogenization in water, preferably, to a final concentration of 1 brain/8 ml, and 1 ml aliquots stored frozen in glass tubes at $-55°$ C. Prior to use, tubes are thawed and placed for about 30 sec in a bath sonicator, following which, in order to block membrane binding by labeled amities, polyethyleneimine is added, preferably, to a final concentration of 0.1%. Alternatively, either dopamine or octopamine may be added to a final concentration of 1 mM. The tubes are then incubated for about 25 min at room temperature (preferably, 25° C.), and kept on ice.

In both the intact tissue and synaptosomal methods, control (sodium-dependent) uptake is defined as the difference in uptake observed in tubes (or intact tissue) incubated with complete buffer minus that seen in tubes (or tissue) incubated with sodium-free buffer (the latter are termed "blanks"). Alternatively, blanks may utilize: (a) an excess (>1 mM) of non-radioactive octopamine, or (b) an excess (>1 mM) of a transporting blocking agent, or (c) during incubation be kept at 0° C. Typically, tubes (or tissue wells) assaying drug effects contain complete buffer with the compound of interest at concentrations from $10^{-12}$M to $10^{-3}$M, or from $10^{-12}$M to $10^{-2}$M. The sodium-dependent uptake in these tubes or tissue pieces containing drug of interest is calculated using the blank noted above and this sodium-dependent uptake then compared with control uptake seen in the absence of any drug.

Although the in vitro assay has been described in considerable detail with reference to certain preferred versions thereof, it will be obvious to a practitioner in the art that modifications may be practiced within the scope of the invention. For example, the pH and the components of the solutions may be modified, and the time and temperature values may be varied. Moreover, following the uptake step, tissue may be separated from unbound radiolabelled octopamine or other phenylethanolamine using an air-driven ultracentrifuge, using a filtration manifold, or by using dialysis. In addition, it is possible to use, as an assay, the binding (and inhibition of binding), to the transporter site, of a radioactively-labelled derivative of a reuptake blocker such as a derivative of chlorethylamine, piperazine, cocaine, or tricyclic antidepressant compounds described herein.

The term "radiolabelled octopamine or other phenylethanolamine" is meant to indicate phenylethanolamines wherein one or more of the atoms thereof are enriched in a radioisotope, or wherein the phenylethanolamine is covalently coupled to a radioisotope label. Examples of such radioisotopes which may enrich the phenylethanolamines of the invention include, but are not limited to $^3$H and $^{14}$C. Examples of radioisotopes which may be used to covalently label the molecule include $^{125}I$, $^{131}I$, $^{32}P$, $^{35}S$, $^{51}Cr$, $^{36}Cl$, $^{57}Co$, $^{58}Co$, $^{59}Fe$, and $^{75}Se$.

The term "octopamine agonist" is meant to indicate a compound which mimics at least some of the effects of octopamine by interaction with the octopamine receptor. For example, an octopamine agonist, like endogenous octopamine, may affect many areas of insect physiology, including carbohydrate metabolism, lipid mobilization, hematocyte function, heart rate, peripheral muscle tension and excitability, and behavior. Thus, overactivation of the octopamine system in insects and acarines by an octopamine agonist may lead to behavioral and physiological abnormalities that have pestistatic and pesticidal consequences.

The pest controlling agents of the present invention can be formulated as dusts, water dispersions, emulsions, and solutions. They may comprise accessory agents such as dust carriers, solvents, emulsifiers, wetting and dispersing agents, stickers, deodorants and masking agents (see, for example, *Encyclopedia of Chemical Technology*, Vol. 13, page 416 et seq.).

Dusts generally will contain low concentration, 0.1–20%, of the compounds, although ground preparations may be used and diluted. Carriers commonly include sulfur, silicon oxides, lime, gypsum, talc, pyrophyllite, bentonites, kaolins, attapulgite, and volcanic ash. Selection of the carrier can be made on the basis of compatibility with the desired pest control composition (including pH, moisture content, and stability), particle size, abrasiveness, absorbability, density, wettability, and cost. The agent of the invention alone or in combination and diluent is made by a variety of simple operations such as milling, solvent impregnations, fusing and grinding. Particle sizes usually range from 0.5–4.0 microns in diameter.

Wettable powders can be prepared by blending the agents of the invention in high concentrations, usually from 15–95%, with a dust carrier such as bentonite which wets and suspends properly in water. 1 to 2% of a surface-active agent is usually added to improve the wetting and suspendibility of the powder.

The pest-controlling agents can also be used in granules, which are pelleted mixtures of the agents, usually at 2.5–10%, and a dust carrier, e.g., adsorptive clay, bentonite or diatomaceous earth, and commonly within particle sizes of 250 to 590 microns. Granules can be prepared by impregnations of the carrier with a solution or slurry of the agents and can be used principally for mosquito larvae treatment or soil applications.

The agents can also be applied in the form of an emulsion, which comprises a solution of the agents in water immiscible organic solvents, commonly at 15–50%, with a few percent of surface active agent to promote emulsification, wetting, and spreading. The choice of solvent is predicated upon solubility, safety to plants and animals, volatility, flammability, compatibility, odor and cost. The most commonly used solvents are kerosene, xylenes, and related petroleum fractions, methylisobutylketone and amyl acetate. Water emulsion sprays from such emulsive concentrates can be used for plant protection and for household insect control.

The agents can also be mixed with baits, usually comprising 1–5% of agents with a carrier especially attractive to insects. Carriers include sugar for house flies, protein hydrolysate for fruit flies, bran for grasshoppers, and honey, chocolate or peanut butter for ants.

The agents can be included in slow release formulations which incorporate non-persistent compounds, insect growth regulators and sex pheromones in a variety of granular microencapsulated and hollow fiber preparations.

The pest controlling agents of the present invention may be applied depending on the properties of the particular pest controlling compound, the habits of the pest to be controlled and the site of the application to be made. It can be applied by spraying, dusting or fumigation.

Doses of the weight of the ingredients may typically vary between 0.001–100 lbs/acre, preferably between 0.001–5 lbs/acre.

Sprays are the most common means of application and generally will involve the use of water as the principal carrier, although volatile oils can also be used. The pest-control agents of the invention can be used in dilute sprays (e.g., 0.001–10%) or in concentrate sprays in which the composition is contained at 10–98%, and the amount of carrier to be applied is quite reduced. The use of concentrate and ultra low volume sprays will allow the use of atomizing nozzles producing droplets of 30 to 80 microns in diameter. Spraying can be carried out by airplane or helicopter.

Aerosols can also be used to apply the pest controlling agents. These are particularly preferred as space sprays for application to enclosures, particularly against flying insects. Aerosols are applied by atomizing amounts of a liquified gas dispersion or bomb but can be generated on a larger scale by rotary atomizers or twin fluid atomizers.

A simple means of pest control agent dispersal is by dusting. The pest controlling agent is applied by introducing a finely divided carrier with particles typically of 0.5–3 microns in diameter into a moving air stream.

Any octopamine reuptake transporter-containing pest is treatable by the formulation of the present invention. These pests include all invertebrate pests, including, but not limited to, round worms (e.g., hookworm, trichina, ascaris); flatworms (e.g., liver flukes and tapeworms); jointed worms (e.g., leeches); mollusks (e.g., parasitic snails); and arthropods (insects, spiders, centipedes, millipedes, crustaceans (e.g., barnacles)). In particular, included among the arthropods are ticks; mites (both plant and animal); lepidoptera (butterflies and moths and their larvae); hemiptera (bugs); homoptera (aphids, scales); and coleoptera (beetles). Also included are spiders; anoplura (lice); diptera (flies and mosquitoes); trichoptera; orthoptera (e.g., roaches); odonta; thysanura (e.g., silverfish); collembola (e.g., fleas); dermaptera (earwigs); isoptera (termites); ephemerids (mayflies); plecoptera; mallophaga (biting lice); thysanoptera; and siphonaptera (fleas); dictyoptera (roaches); psocoptera (e.g., booklice); and certain hymenoptera (e.g., those whose larva feed on leaves).

Having now generally described this invention, the same will become better understood by reference to certain specific examples which are included herein for purposes of illustration only and are not intended to be limiting unless otherwise specified. All patents and publications cited herein are fully incorporated by reference herein in their entirety.

EXAMPLES

In Vitro Assay For Determination Of Transporter Inhibitory Activity Of Compounds Of Interest The question of whether a given compound is an inhibitor of octopamine neuronal transport can be readily determined by measuring the uptake of radioactive octopamine or similar phenylethanolamine into membrane (broken cell) preparations derived from insect or other invertebrate nerve tissue. To prepare membrane (broken cell) preparations, insect ventral nerve cord and brain ganglia from specimens of *Periplaneta americana, Manduca sexta*, or other insect or invertebrate pest are removed and homogenized in a teflon-glass homogenizer in 50 volumes of 0.32M sucrose and then centrifuged at high speed (typically 100,000×g) for 30 minutes to obtain a membrane pellet. The pellet is suspended in insect Ringers solution containing sodium chloride at 0° C. and at a concentration of approximately 10 mg tissue per ml. Optionally, the Ringers may also contain 2 mM ascorbic acid and an inhibitor of monamine oxidase, such as pargyline. 0.2 ml or similar-sized aliquots of the membrane tissue suspension are added to $^3$H-octopamine or similar phenylethanolamine (typically 10–40 mCi/mmol) in test tubes to a final concentration of 1 micromolar of the radioactive amine. Control tubes contain no additional compounds. Other tubes contain the compound of interest to be tested at concentrations of from $10^{-12}$M to $10^{-2}$M. In addition, there are "blank" control tubes in which the sodium chloride in the insect Ringers solution has been substituted with Tris buffer or choline chloride. Alternatively, blanks may utilize: (a) an excess (>1 mM) of non-radioactive octopamine, or (b) an excess (>1 mM) of a transporting blocking agent, or (c) during incubation (see below), be kept at 0° C.

Alternatively, the radioactive compound may be a radioactively-labelled derivative of a reuptake blocker such as a derivative of chlorethylamine, piperazine, cocaine, or tricyclic antidepressant compounds described herein. In this case, inhibition (by the compound of interest) of binding to the transporter site is measured and is equivalent.

To measure octopamine transport (or "uptake") into membranes (or, binding of a reuptake blocker to the transporter site), the tubes are incubated at 20°–35° C. for 10–30 minutes, and then the contents of each tube are transferred to glass fiber filters on a filtration manifold and washed quickly under low vacuum with aliquots of ice-cold insect Ringers solution. The filters are then dried and the radioactivity remaining in the filters quantitated by liquid scintillation counting. Alternatively, the membranes may be washed by two cycles of high speed centrifugation, and the radioactivity in the final pellet quantitated by liquid scintillation counting.

After washing, radioactivity counts in the blank are subtracted from the radioactivity quantitated in the other tubes. Radioactivity remaining in the washed control membranes represents baseline phenylethanolamine transport (or, in the case of a labelled transporter blocker, baseline binding to the transporter). The radioactivity in the washed membranes from the tubes containing the compound of interest is plotted relative to control transport (or binding), and the degree of inhibition relative to control uptake is noted. To determine if the compound of interest has substantial inhibitory activity toward octopamine transport, the maximum percent decrease from control seen over the range of concentrations ($10^{-12}$M to $10^{-2}$M, or $10^{-2}$M to $10^{-3}$M) tested is determined. If this value is between 25% and 100%, then the compound is an active inhibitor of transport.

In a more preferable in vitro assay, the question of whether a given compound is an inhibitor of octopamine neuronal transport is readily determined by measuring the uptake of radioactive octopamine or other phenylethanolamine into intact tissue or synaptosomal-containing preparations from insect or other invertebrate nerve tissue.

To measure uptake into intact tissue, hemisected cerebral ganglia and thoracic ganglia are removed from the insect of interest (e.g., *Periplaneta americana*, Blaberus, *Manduca sexta* or other invertebrate pest) and pre-incubated at 28° C. for 15 min in a modified insect saline solution typically containing: 10 mM D-glucose; 130 mM NaCl; 8 mM KCl; 2 mM CaCl$_2$; 2 mM MgCl$_2$; 2.5 mM K$_2$CO$_3$; 2 mg/ml ascorbic acid; and 50 mM HEPES buffer. The pH is adjusted with NaOH to pH 7.2 (at 31° C.), which gives a final sodium concentration of about 155–160 mM and an osmolality of about 350–355. In order to measure sodium-dependent uptake, some ganglia are pre-incubated in a sodium-free insect saline solution in which sodium chloride is omitted and an equiosmolar amount of Tris buffer (17.6 g Tris HCl and 4.54 g Tris base per liter) added ("sodium-free saline solution"). Both saline solutions may also contain 1 µM pargyline HCl. After preincubation, tissue is transferred with fine forceps to wells in a 24 well/plate tissue culture dish. Each well contains just enough insect saline solution (approx. 400 µl/well) to barely cover the tissue pieces, thereby facilitating oxygenation under room atmospheric conditions. Some wells contain the compound to be assayed while others contain sodium-free saline solution. Tritiated octopamine or other phenylethanolamine is present in all wells at a final concentration of approximately 1 µM and 5 µCi/ml. Following incubation for 15 min at 28° C., tissue pieces are transferred by forceps to 10 ml of ice-cold insect saline solution (or sodium-free insect saline solution), gently agitated for 30 sec, then transferred to a second 30 sec ice-cold wash, prior to final transfer to scintillation vials, where tissue is dissolved overnight in 0.5 ml of 0.5N NaOH, following which radioactivity is quantitated and sodium-dependent uptake calculated on the basis of pmol amine/mg protein.

For example, in a typical experiment, the uptake of octopamine was measured in intact hemi-cerebral ganglia (i.e., cerebral ganglia lacking optic lobes) obtained from Blaberus. In control tissue, total uptake was determined to be 13.6±1.7 pmol/mg protein (±S.E.M. of triplicate determinations). Sodium-dependent uptake constituted 58% of the total uptake, while the remaining 42% uptake was due to sodium-independent uptake. In the presence of 100 µM cocaine, total uptake decreased to 9.6 ±1.4 pmol/mg protein (±S.E.M. of triplicate determinations), representing an inhibition of 51%.

To measure uptake into synaptosomal preparations, the ganglia from the insect of interest is rinsed briefly in cold 0.32M sucrose solution containing 15 mM Tris maleate pH 7.2, and transferred in 1 ml of sucrose/Tris (usually 50 mg tissue/ml) to a 2 ml-sized Teflon-glass homogenizer with 0.25 mm clearance. (A higher sucrose concentration (0.5–0.8M) may improve synaptosomal yield in some species.) Tissue is then gently homogenized on ice at 200 rpm with 10 up and down strokes. The homogenate is transferred to a 12 ml conical plastic tissue-culture tube, 9 ml of cold sucrose/Tris added, and the mixture centrifuged at 800×g for 10 min in the cold in a swinging bucket rotor. The P1 pellet is discarded, and the supernatant transferred to a 10 ml round-bottom thick-walled centrifuge tube and recentrifuged at 40,000×g for 30 min in a fixed angle rotor. The resulting P2 pellet is resuspended by gentle trituration in sucrose/Tris (50 mg original wet weight/ml), transferred to the original Teflon-glass homogenizer, and gently rehomogenized, by hand, to a uniform suspension. This synaptosomal fraction (a 10X stock concentration for most studies) is then stored on ice until use in uptake studies.

Uptake is typically measured in 14×89 mm clear, thin-walled, high speed plastic centrifugation tubes. 140 μl of modified insect saline solution or sodium-free saline solution (described above) is added to each tube. Ascorbic acid (2 mg/ml) may be present to reduce oxidation of amines. Pargyline (1 μM) may also be added to inhibit monoamine oxidase (MAO), even though, in insects, it is unclear whether or not MAO plays a major role in enzymatic degradation of monoamines. Tubes are cooled to 4° C., tritiated octopamine or other phenylethanolamine (typically 10–40 Ci/mmol, final concentration 0.5–5 μM in a volume of 20 μl) and drugs (in a volume of 20 μl of water) added, and tubes preincubated at 31° C. for 5 min. The uptake incubation (10 min at 31° C.) is started by the addition of 20 μl of 10X synaptosomal fraction in 0.32M sucrose/Tris maleate. Uptake incubation is terminated by pipetting the contents of the incubation tubes to new 14×89 mm tubes filled with 4.5 ml of ice-cold incubation saline solution (or sodium-free saline solution) containing 1 mM phentolamine mesylate and 75 μl of tissue carrier fraction. An additional 4.5 ml of ice-cold incubation saline solution (or sodium-free saline solution) with phentolamine is added and tubes are centrifuged for 20 min at 40,000 ×g and the supernatant carefully aspirated under low vacuum with a pasteur pipette. The pellet is left undisturbed, but rapidly and gently washed with 4 ml of the appropriate ice-cold buffer for 30 sec. Buffer is carefully aspirated and the intact pellet washed gently again with 2 ml of ice-cold buffer for 30 sec. Following aspiration of the wash, any remaining droplets on the tube walls or bottom are meticulously aspirated, then 0.8 ml of 0.3N NaOH is added directly to the bottom of the tube, and the tube left undisturbed (not vortexed) for several hours to dissolve the pellet. The pellet is then gently triturated (not vortexed) and transferred to a scintillation vial for counting of uptake.

The tissue carrier fraction noted above is prepared from frozen rat brains which are thawed on ice, the brainstem and cerebellum removed, and the cerebrum thoroughly homogenized in distilled water (1 brain/10 ml) in a glass/glass homogenizer. Homogenate is centrifuged at 40,000×g for 20 min, supernatant discarded, pellet resuspended in 10 ml of distilled water and again centrifuged. The final pellet is resuspended by homogenization in water to a final concentration of 1 brain/8 ml, and 1 ml aliquots stored frozen in glass tubes at −55° C. Prior to use, tubes are thawed and placed for 30 sec in a bath sonicator, following which, in order to block membrane binding by labeled amines, polyethyleneimine is added to a final concentration of 0.1%, or either dopamine or octopamine is added to a final concentration of 1 mM. Tubes are incubated for 25 min at 25° C., and then kept on ice.

For example, in a typical experiment, the uptake of octopamine was measured in synaptosomal-containing preparations obtained from cockroach nervous system. Control sodium-dependent uptake was about 8.4 pmol/mg protein. In the presence of 10 μM cocaine, uptake was inhibited by about 25%, while in the presence of 100 μM cocaine, uptake was inhibited by about 68%.

In both the intact tissue and synaptosomal methods, control (sodium-dependent) uptake is defined as the difference in uptake observed in tubes (or intact tissue) incubated with complete buffer minus that seen in tubes (or tissue) incubated with sodium-free buffer (the latter are termed "blanks"). Alternatively, blanks may utilize: (a) an excess (>1 mM) of non-radioactive octopamine, or (b) an excess (>1 mM) of a transporting blocking agent, or (c) during incubation be kept at 0° C. Typically, tubes (or tissue wells) assaying drug effects contain complete buffer with the compound of interest at concentrations from $10^{-12}$M to $10^{-3}$M, or from $10^{-12}$M to $10^{-2}$M. The sodium-dependent uptake in these tubes or tissue pieces containing drug of interest is calculated using the blank noted above and this sodium-dependent uptake then compared with control uptake seen in the absence of any drug. To determine if the compound of interest has substantial inhibitory activity toward octopamine transport, the maximum percent decrease from control seen over the range of drug concentrations ($10^{-12}$M to $10^{-3}$M, or $10^{-12}$M to $10^{-2}$M) tested is determined. If this decrease is between 25% and 100% of the control value, then the compound is an active inhibitor of transport.

In vivo Methods

Method 1-Antifeeding Assay and Ovacidal Assay

To test the pesticidal and pestistatic effects of some of the disclosed compounds, the effects on the feeding behavior of tobacco hornworms (*Manducca sexta*) were investigated. This species is one of the several types of insects particularly susceptible to octopamine type insecticides. The ease of rearing this species from eggs in the laboratory and the ability to maintain them on artificial media, made it possible to test compounds on large numbers of larvae of the same age.

For testing, single tomato leaves were placed in a closed container, with stems hydrated by means of a small, 3 ml water-filled bottle. Compounds dissolved in water or methanol were sprayed on the tomato leaves with an ultra fine atomizer. Six 3-day-old larvae were placed on each leaf, allowed to teed for 24–108 hours, and then the percentage of leaf remaining was determined by planimetry, weight, or "blind" visual observation. An active compound was one which resulted in an increase in percentage of leaf remaining, compared with control.

Test agents were tested for ovicidal activity by dipping groups of 10–50 Manducca eggs in drug solutions for 60 seconds and then determining the percentage of eggs which produced viable larvae. Alternatively, the eggs may be sprayed with the test agent and then placed on artificial media to hatch. A compound with active ovicidal activity was one which decreased the percentage of eggs hatched, relative to control.

Method 2-Firely Lantern Assay

To measure the effects of drugs on firefly light emission, an isolated tail (terminal 3 abdominal segments containing the light organ) of a fresh adult *P. pyralis* male was mounted on a 30-g stainless steel needle and placed at the focal point of an optical system connected to a photometer-photomultiplier-chart recorder combination (see Nathanson, J. A., Characterization of octopamine-sensitive adenylate cyclase: Development of a potent and selective class of octopamine-2 receptor agonists with toxic effects in insects, *Proc. Natl. Acad. Sci. U.S.A.* 82: 599-603 (1985)). Drug (dissolved in insect saline, see Carlson, A.D., Effect of adrenergic drugs on the lantern of the larvae of the Photinus firefly, *J. Exp. Biol.* 48: 381-387 (1968)) was injected (3-5 µl) into the abdominal cavity dorsal to the lantern and light emission was recorded for 45 minutes or until it peaked, following which the next (larger) dose of drug was injected. In the case of animals injected with drugs other than octopamine, following the last dose, 10 mmol of octopamine (a maximally effective dose) was injected. Light production is expressed as radiance, each unit approximately equal to 1.6 nanowatts, as measured in a solid angle of 0.033 steradiants. Nathanson, J. A., Phenyliminoimidazolidines: Characterization of a Class of Potent Agonists of Octopamine-sensitive Adenylate Cyclase and Their Use in Understanding the Pharmacology of Octopamine Receptors, *Molec. Pharmacol.* 28: 254-268 (1985).

Method 3-Antilarval Activity of Cocaine

Five to ten 2-5-day old mosquito larvae, reared from eggs, were placed in small bottles containing 3 ml of water, 2 ml of air space, and a perforated cap open to the air. The compound of interest was dissolved in water or appropriate solvent and added to make a final concentration of from 0.00001 to 1%. The bottles were capped and observed at daily intervals for the number of living larvae, pupae, and emerging adults. After two weeks, the final number of adults emerging as a percentage, relative to control, is plotted as a function of drug concentration.

Example 1

Feeding Inhibition of *M. sexta* on cocaine-sprayed tomato leaves

Figure 2:
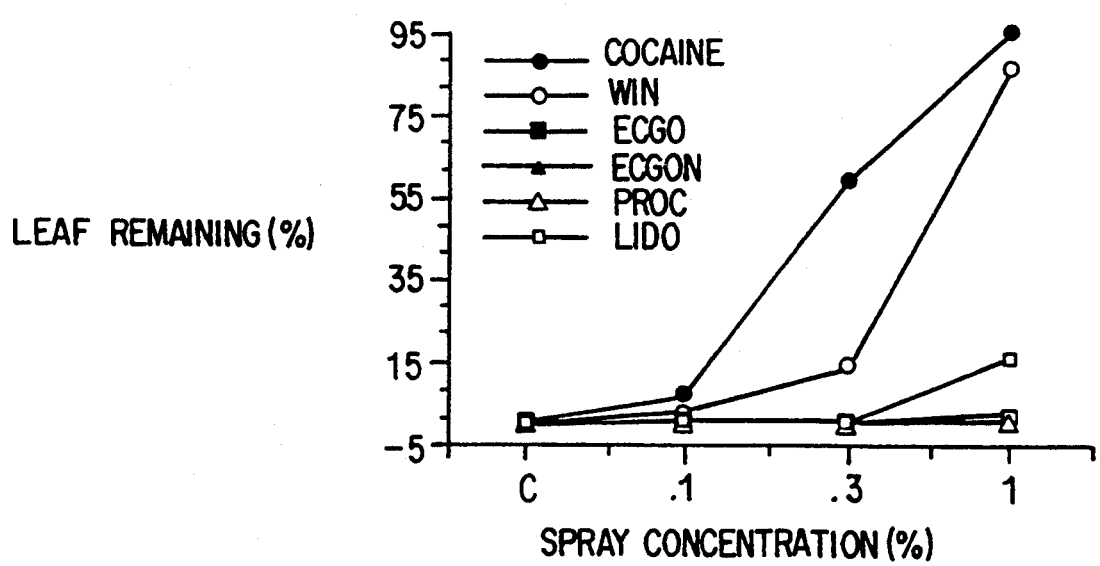
FIG. 2 is a graph representing the antifeeding effect of the application of cocaine analogs and local anesthetics, as a reuptake inhibitor versus applied concentration. Data for cocaine, WIN 35,428 (CFT naphthalene disulfonate((-)-2-beta-carbomethoxy-3-beta-(4-fluorophenyl)tropane-1,5-naphthalene disulfonate), ecgonine hydrochloride, ecgonidine methyl ester mesylate, procaine, and lidocaine are shown. Antifeeding inhibition was measured according to the in vivo assay for tomato leaves, described infra under "In vivo Methods." At high (approximately 1%) concentrations, the % leaf remaining was approximately 90 and 95% for WIN 35,428 and cocaine, respectively, demonstrating a marked antifeeding effect for the cocaine-type class of compounds. Of the local anesthetics only lidocaine showed any activity (15% inhibition), demonstrating that local anesthetics are not necessarily indicated for antifeeding activity.

First instar *M. sexta* larvae were placed upon tomato leaves presprayed with various concentrations of cocaine. After a few minutes of exposure to cocaine-sprayed leaves, larvae displayed marked behavioral abnormalities, including rearing, tremors, and walk-off activity. These behaviors increased in intensity as larvae began to feed and, at higher concentrations of cocaine, animals died after 48-72 hours. As a result, leaves were protected, and FIG. 2 shows the dose-response relationship on inhibition of feeding that was observed. Cocaine and the cocaine derivative WIN 35,428 (CFT Naphthalene disulfonate((-)-2-beta-carbomethoxy-3-beta-(4-fluorophenyl) tropane-1,5-naphthalene disulfonate) (Research Biochemicals Inc., Natick, Mass.) (Madras, B., et al., *Mol. Pharmacol.* 36:518 (1989))) show a marked inhibition on leaf feeding. At 1% spray concentration, cocaine and WIN 35,428 show 90 and 95% leaf remaining, respectively. Ecgonine hydrochloride ((-)-beta-hydroxy-1-alpha-H, 5-alpha-H-tropane-2-beta-carboxlic acid hydrochloride) and Ecgonidine methyl ester mesylate ((1 R)-8-methyl-8-azabicyclo[3,2,1]oct-2-ene-2-carboxylic acid methyl ester mesylate) displayed no antifeeding effect, suggesting that both the tropane ring and the benzoyl substituent are necessary for activity. Control experiments using procaine and lidocaine showed that leaf protection was not due to local anesthetic effects, an observation consistent, also, with the fact that larvae exposed to cocaine initially demonstrated hyperactivity rather than hypoactivity. As will be described in the examples which follow, the pest-controlling mechanism of action of cocaine and the other reuptake blockers is through their action on blocking the reuptake of OA (rather than some other amine).

Example 2

Feeding Inhibition of Known Amine Reuptake Blockers

Figure 3:
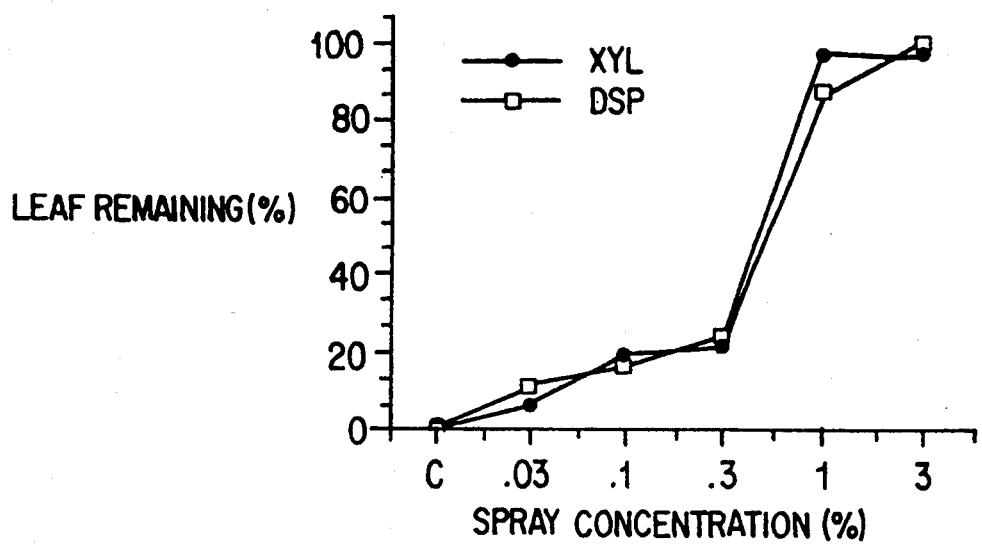
FIG. 3 is a graph demonstrating the antifeeding effect of the application of chloroethyphenyl amine reuptake inhibitors versus applied concentration. Data for Xylamine and DSP-4 are shown. Antifeeding inhibition was measured according to the in vivo assay for tomato leaves, described infra under "In vivo Methods." At high (approximately 1-3%) concentrations, the % leaf remaining approached 100%, demonstrating a marked antifeeding effect for this class of compounds.
Figure 4:
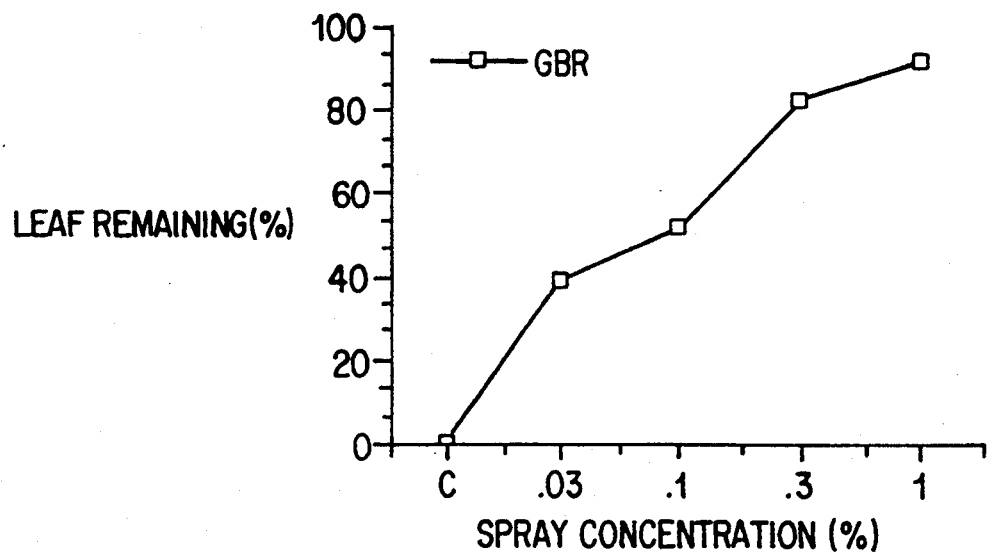
FIG. 4 is a graph demonstrating the antifeeding effect of the application of GBR-type reuptake inhibitors versus applied concentration. Data for GBR 12909 are shown. Antifeeding inhibition was measured according to the in vivo assay for tomato leaves, described infra under "In vivo Methods." At high (approximately 1%) concentrations, the % leaf remaining approached 95%, demonstrating a marked antifeeding effect for this class of compounds.
Figure 5:
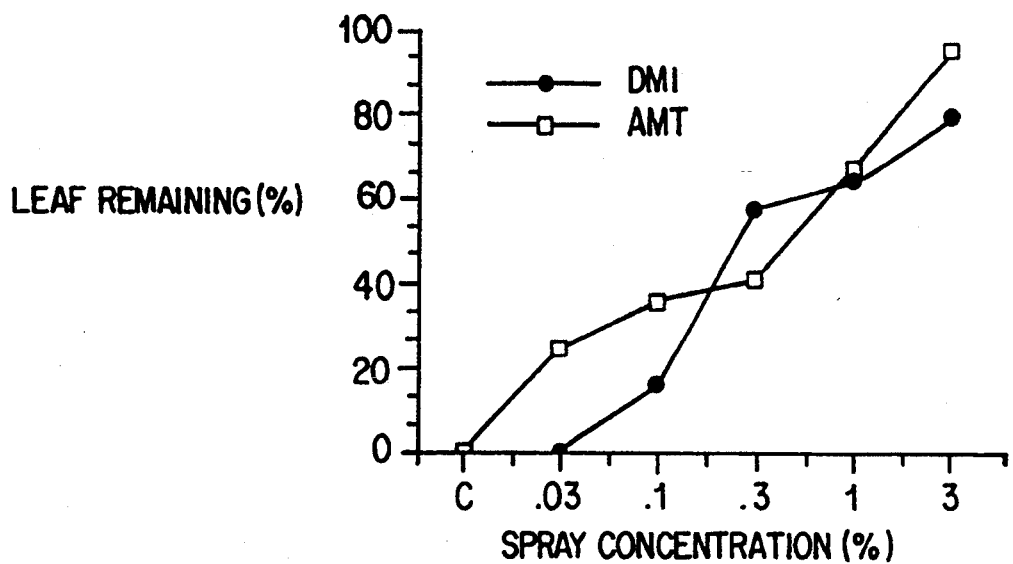
FIG. 5 is a graph demonstrating the antifeeding effect of the application of tricyclic antidepressant-type reuptake inhibitors versus applied concentration. Data for desmethylipramine (DMI) and amitriptyline (AMT) are shown. Antifeeding inhibition was measured according to the in vivo assay for tomato leaves, described infra under "In vivo Methods." At high (approximately 3%) concentrations, the % leaf remaining approached 80 and 100%, respectively, demonstrating a marked antifeeding effect for this class of compounds.
Figure 6:
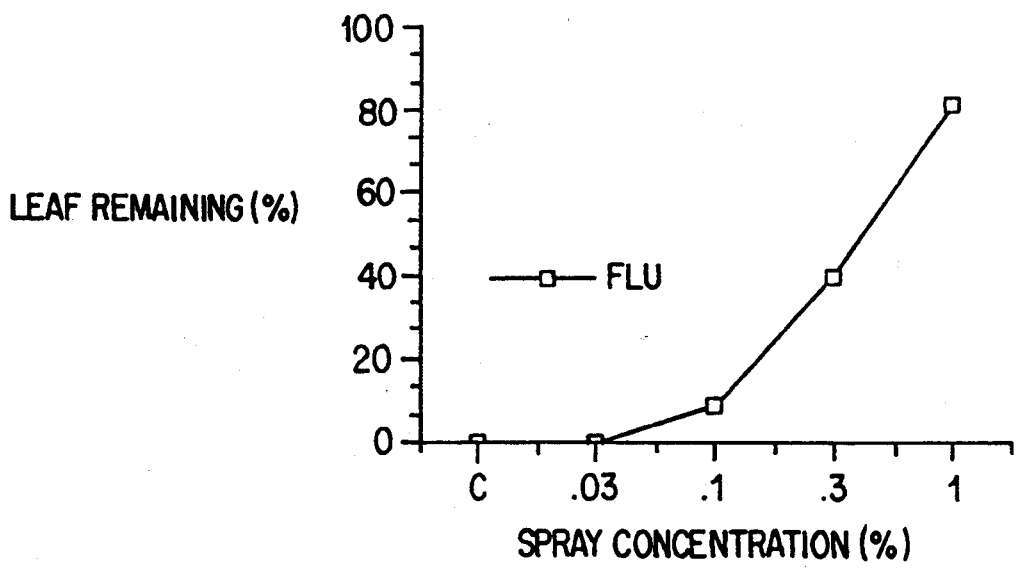
FIG. 6 is a graph demonstrating the antifeeding effect of the application of fluoxetine, an atypical antidepressant, as a reuptake inhibitor versus applied concentration. Antifeeding inhibition was measured according to the in vivo assay for tomato leaves, described infra under "In vivo Methods." At high (approximately 1%)concentrations, the % leaf remaining approached 85%, demonstrating a marked antifeeding effect for this class of compounds.

Pharmacological evidence from vertebrates supports the presence of distinct reuptake sites (amine transporter proteins) tier DA, NE, and serotonin (5-HT), as discussed infra. The potential insect antifeeding effects of several other known amine reuptake blockers, representing three more classes of compounds with varying degrees of selectivity toward DA, NE, and 5-HT, were examined for their possible insecticidal activity. Six compounds had antifeeding effects, including desmethylimipramine (DMI) (a better NE than 5-HT uptake blocker), amitriptyline (AMT) (a better 5-HT than NE reuptake blocker), xylamine (XYL) and DSP-4 (both primarily NE uptake blockers), fluoxetine (FLU) (primarily a 5-HT reuptake blocker), and GBR 12909 (a relatively selective DA reuptake blocker). FIG. 3 shows the two chloroethylphenylamine compounds Xylamine and DSP-4. Antifeeding inhibition was measured according to the in vivo assay for tomato leaves, described infra under "In vivo Methods." At high (approximately 1-3%) concentrations, the % leaf remaining approached 100%, demonstrating a marked anti feeding effect for the chloroethylphenylamine class of compounds. FIG. 4 shows the effect of the aryl-1,4-dialk(en)yl piperazine compound GBR 12909 (1-(2-[bis-(4-fluorophenyl)methoxy]ethyl)-4-(3-phenyl-2-propenyl)piperazine) (Research Biochemicals, Inc., Natick, Mass.). At high (approximately 1%) concentrations, the % leaf remaining approached 95%, demonstrating a marked antifeeding effect for this class of compounds. FIG. 5 shows the antifeeding effect of two representative tricyclic antidepressants, desmethylimipramine (DMI) and amitriptyline (AMT) (Sigma Chemical, St. Louis, Mo.). At high (approximately 3%) concentrations, the % leaf remaining approached 80 and 100%, respectively. FIG. 6 depicts the leaf antifeeding effect of the atypical antidepressant fluoxetine. At high (approximately 1%) concentrations, the % leaf remaining approached 85%, demonstrating a marked antifeeding effect for this class of compounds. In other experiments (not shown), the NE and DA uptake blocker, mazindol, exerted no antifeeding activity.

When the rank order of these various compounds for insect antifeeding potency is compared with their relative potency at blocking DA reuptake into rat brain synaptosomes (Table 1) (Andersen, P., *J. Neurochem.* 48: 1887-96 (1987); Bonnet, J., et al., *Eur. J. Pharmacol.* 126: 211-22 (1986); Berger, P., et al., *Eur. J. Pharmacol.* 107: 289-90 (1985)), it is clear that the pharmacology differs in the two instances.

TABLE 1

RANK ORDER EFFECT ON BLOCKING DA UPTAKE
GBR >> MAZ > COC >> DMI = AMT = FLUOX
RANK ORDER ANTIFEEDING EFFECT IN MANDUCA
GBR > COC = DMI = AMT > DSP = XYL =

TABLE 1-continued

FLUOX >>MAZ
RANK ORDER EFFECT ON BLOCKING NE UPTAKE
MAZ > DMI >> AMT = GBR = COC
RANK ORDER EFFECT ON BLOCKING 5-HT UPTAKE
FLUOX > AMT >> DMI = COC > GBR > MAZ

Thus, either the pharmacological selectivity of the DA transporter of insects is different from that in mammals or these drugs are affecting the uptake of some other amine. Table 1 shows that the rank order potency of antifeeding effect in Manduca is also different from the relative selectivity of these compounds in blocking NE uptake (Richeson and Pfenning, *Eur. J. Pharmacol.* 104: 277-286 (1984); Pacholczyk, T., et al., *Nature* 350: 350-52 (1991)) or serotonin uptake (Richeson and Pfenning, ibid.; Blakely, R., et al., *Nature* 354: 66-70 (1991)), results which suggest that the antifeeding activity observed is not due to an effect on NE or 5-HT uptake.

Figure 7:
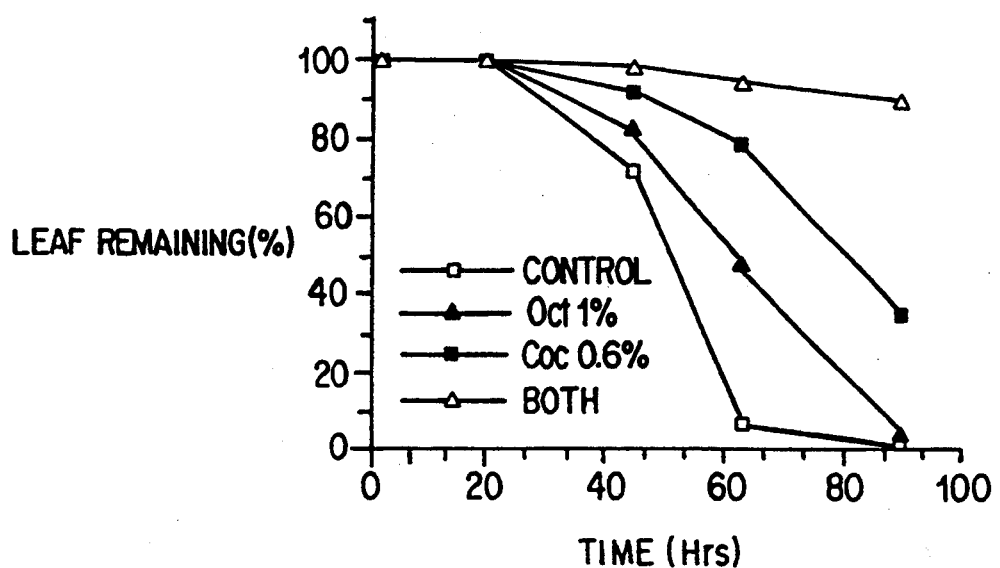
FIG. 7 is a graph representing the antifeeding effect of the application of cocaine and OA, individually and in combination, as % leaf remaining versus time. Data for 0.6% cocaine alone, 1% OA alone, both, and a control, are shown. Antifeeding inhibition was measured according to the in vivo assay for tomato leaves, described infra under "In vivo Methods." At 90 hours, the % leaf remaining was approximately 5% and 35% for 1% OA and 0.6% cocaine, respectively, while the combination shows 90% leaf remaining. This demonstrates a marked synergistic antifeeding effect for the combination over the individual components.
Figure 8:
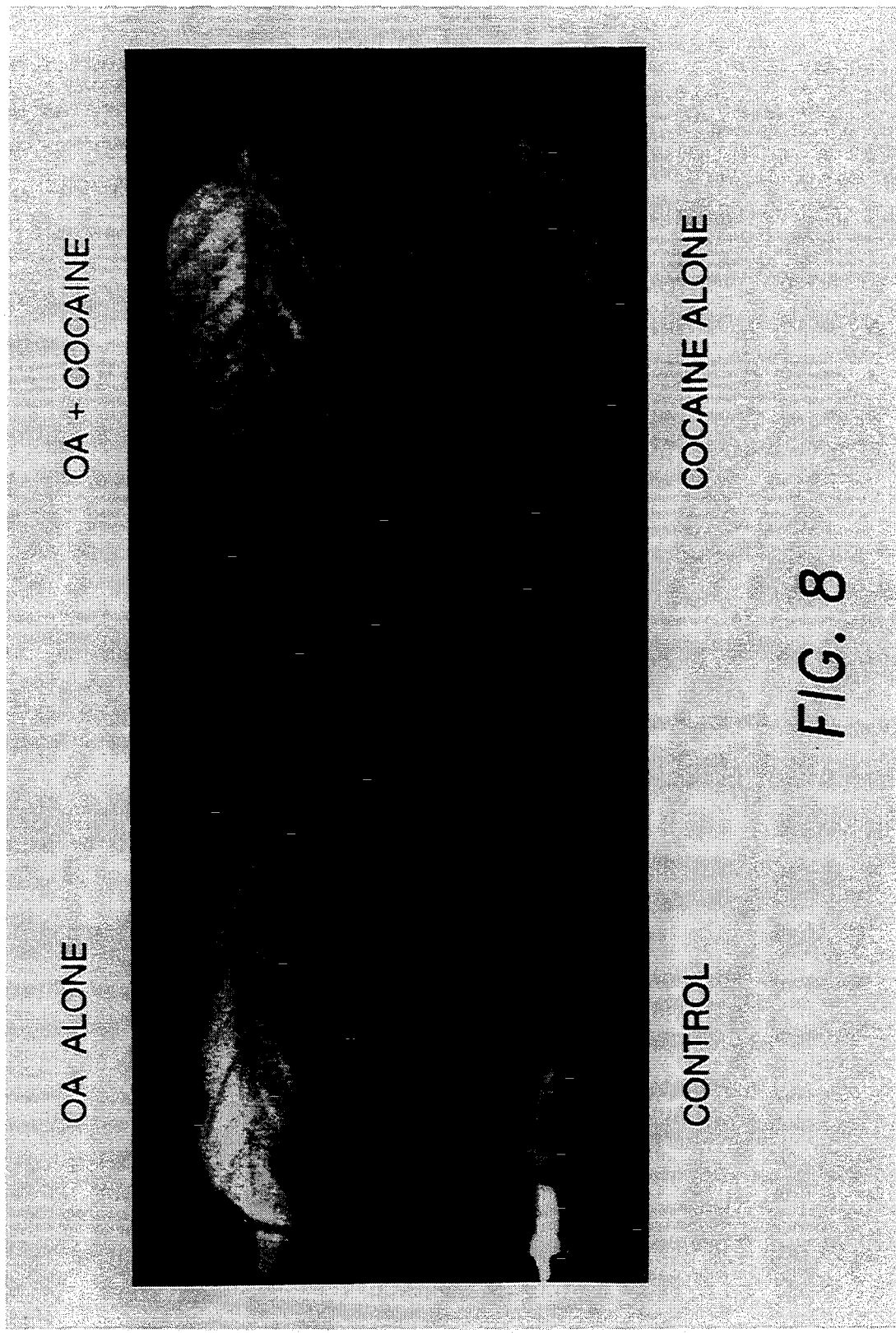
FIG. 8 is a photograph of four tomato leaves after application of OA and cocaine as described under FIG. 7. It shows that a concentration of OA which by itself was only partially effective in protecting leaves, when added to a partially effective concentration of cocaine, resulted in complete leaf protection.

Of interest, the behavioral effects of these compounds in Manduca are similar, not only to the effects of cocaine, but also to the adverse behavioral effects that we have previously observed with OA receptor agonists. Thus, if the antifeeding effects of the reuptake blockers are not due to their action on DA, NE or 5-HT, it is likely that the compounds are working through a blockade of OA reuptake, thereby augmenting OA neurotransmission and functionally acting as OA agonists. This will be demonstrated below in Examples 3-5 (FIGS. 7-8). Work done over a decade ago by Evans (Evans, P. D., *J. Neurochem.* 30: 1015-1022 (1978)) showed the presence, in cockroach nerve cord, of high affinity uptake for OA which is blockable by DMI. Unfortunately (in part due to the relative lack of selectivity of blockers then available), pharmacological characterization of this site was, at the time, insufficient to determine whether the characteristics of the OA uptake were distinct from those of mammalian amine reuptake sites.

Example 3

Synergistic Antifeeding Effect of Octopamine Administered with Cocaine

FIG. 7 shows a concentration of OA, which by itself, was only partially effective in protecting leaves, and when added to a partially effective concentration of cocaine, resulted in complete leaf protection. Data for 0.6% cocaine alone, 1% OA alone, both, and a control, are shown. Antifeeding inhibition was measured according to the in vivo assay for tomato leaves, described infra under "In vivo Methods." At 90 hours, the % leaf remaining was approximately 5% and 35% for 1% OA and 0.6% cocaine, respectively, while the combination shows 90% leaf remaining. This demonstrates a marked synergistic antifeeding effect for the combination over the individual components when tested separately. FIG. 8 is a photograph of four tomato leaves after application of OA and cocaine as just described. It shows that a concentration of OA which by itself was only partially effective in protecting leaves, when added to a partially effective concentration of cocaine, resulted in complete leaf protection.

Evidence indicating a lack of involvement of DA was obtained from a similar experiment in which DA, alone (at doses up to twice that of OA), caused no antifeeding effects in Manduca and addition of DA to cocaine caused no further increase in antifeeding effect. Compared to OA, NE and 5-HT (when used alone) were also significantly weaker than OA as antifeeding agents.

Example 4

Antifeeding Effect of Cyproheptadine

Figure 9:
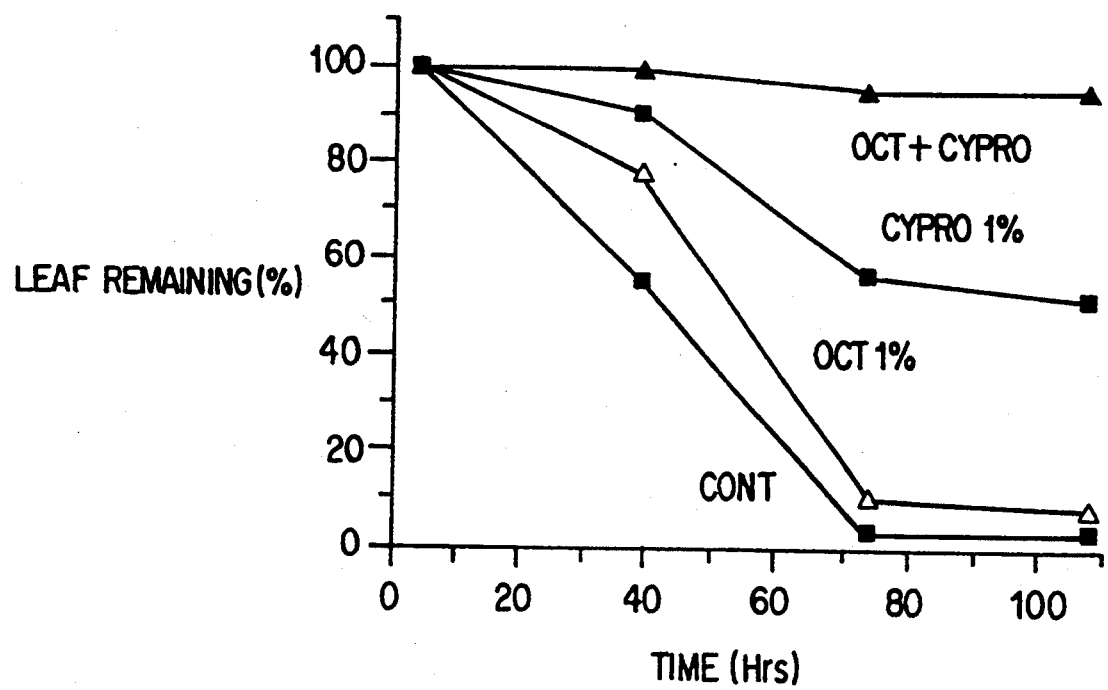
FIG. 9 is a graph representing the antifeeding effect of the application of OA and the known octopamine receptor blocker cyproheptadine, (see J. A. Nathanson, Trace Amines and the Brain; Eds. Marcel Dekker, pp. 161-190 (1976); Nathanson, J. A., et al., Proc. Natl. Acad. Sci. U.S.A. 71: 7797-7801 (1974)) individually and in combination, as % leaf remaining versus time. Data for 1% octopamine alone, 1% cyproheptadine alone, both, and a control, are shown. Antifeeding inhibition was measured according to the in vivo assay for tomato leaves, described infra under "In vivo Methods." At 108 hours, the % leaf remaining was approximately 10% and 55% for 1% OA alone and 1% cyproheptadine alone, respectively, while the combination shows greater than 95% leaf remaining. This demonstrates a marked synergistic antifeeding effect for the combination over the individual compounds.

Cyproheptadine is an antagonist of OA-activated insect adenylate cyclase (J. A. Nathanson, *Trace Amines and the Brain*: Eds. Marcel Dekker, pp. 161-190 (1976); Nathanson, J. A., et al., *Proc. Natl. Acad. Sci. U.S.A.* 71: 7797-7801 (1974)). FIG. 9 is a graph representing the antifeeding effect of the application of octopamine and the known octopamine receptor blocker cyproheptadine,(see J. A. Nathanson, supra; Nathanson, J. A., et al., supra) individually and in combination, as % leaf remaining versus time. Data for 1% octopamine alone, 1% OA alone, both, and a control, are shown. Antifeeding inhibition was measured according to the in vivo assay for tomato leaves, described infra under "In vivo Methods." At 108 hours, the % leaf remaining was approximately 10% and 55% for 1% OA alone and 1% cyproheptadine alone, respectively, while the combination shows greater than 95% leaf remaining. This demonstrates a marked synergistic antifeeding effect for the combination over the individual compounds.

FIG. 9 shows, surprisingly, that cyproheptadine alone inhibited feeding of Manduca and that, even more perplexing, instead of blocking, potentiated the antifeeding effects of OA. This unexpected action can now be explained by the structure of cyproheptadine which is virtually identical to that of amitriptyline, an amine reuptake blocker. In fact, the literature indicates that cyproheptadine can block amine reuptake (Evans, P. D., *J. Neurochem.* 30: 1015-1022 (1978)). Thus, behaviorally, this compound's potentiating effect on reuptake is greater than its effect on OA receptor blockade, not only explaining its antifeeding activity but also providing additional support for using OA uptake as a potential target for pesticides and pestistatics.

Example 5

Potentiation of OA Stimulation in the Firefly Lantern

Figure 10:
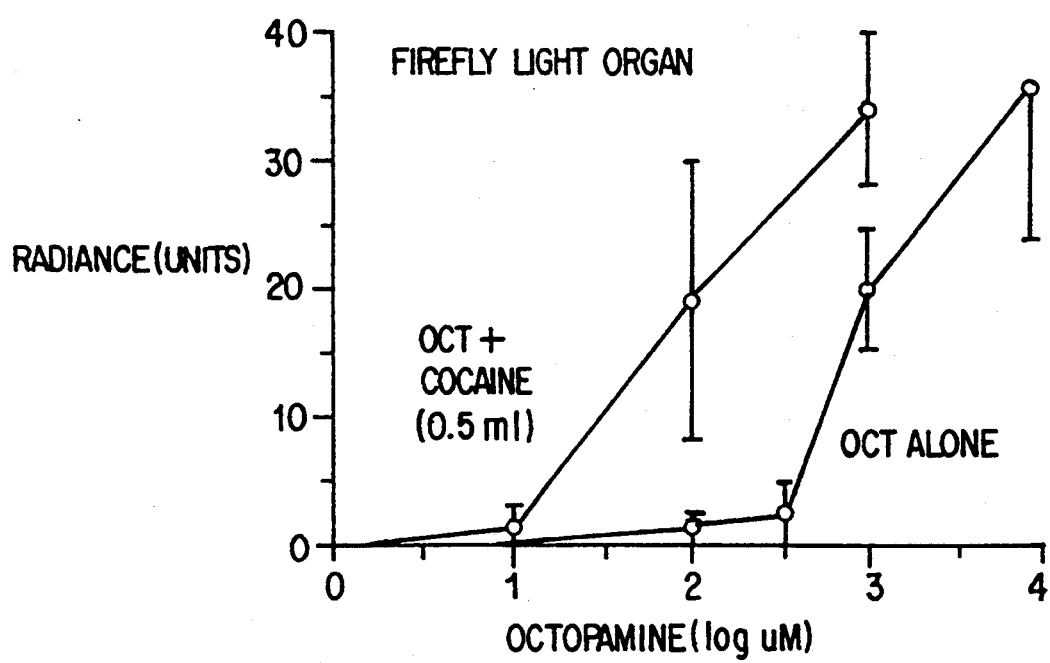
FIG. 10 is a graph of the radiance emitted from OA-stimulated Firefly lanterns plotted versus octopamine concentration. Shown are data for OA alone and OA applied with cocaine.

Additional and more direct evidence for the ability of cocaine to potentiate OA neurotransmission has come from an experiment carried out using the OA-mediated regulation of light emission in the firefly lantern. This assay is described infra under "In vivo Methods." As mentioned, this system is purely octopaminergic without any evidence of membrane receptors for DA, 5-HT or NE. FIG. 10 shows that injection of OA into isolated firefly tails results in a dose-dependent increase in light emission. Simultaneous injection of a fixed dose of cocaine potentiates this action of OA, causing a leftward shift in the OA dose-response curve by a factor of about 10.

These experiments not only support an action of cocaine on OA transmission but, because they were run with zero Ca++/high Mn++, are also consistent with the expected effect of cocaine on neurotransmitter reuptake, rather than release. (These ionic conditions prevent synaptic release (J. A. Nathanson, *Trace Amines and the Brain*; Eds. Marcel Dekker, pp. 161-190 (1976); Nathanson, J. A., *Mol. Pharmacol.* 28: 254-268 (1985)).

Example 6

Effect of Cocaine on Mosquito Larvae

Figure 11:
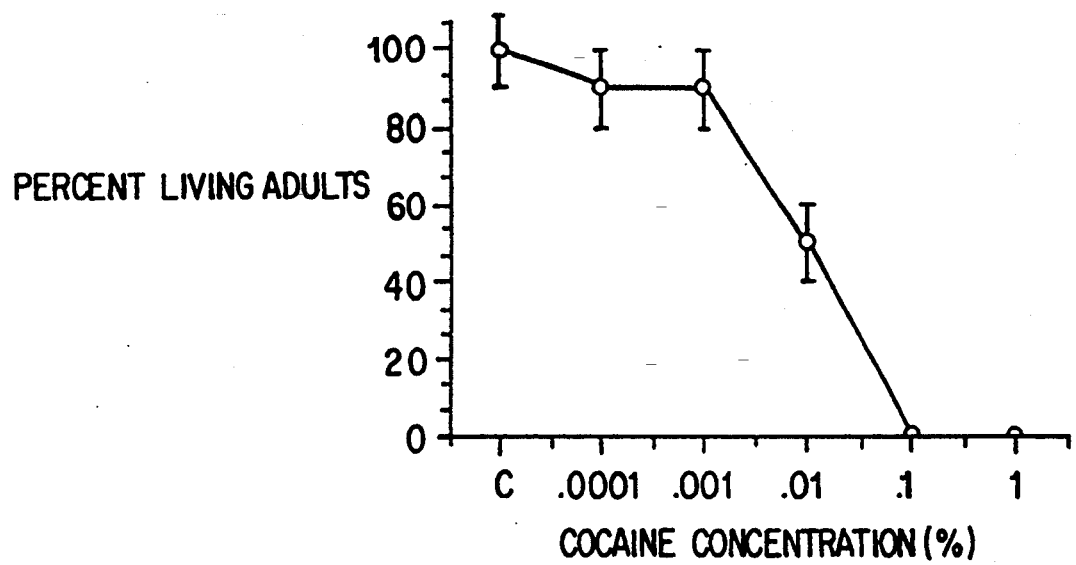
FIG. 11 is a graph of the effect of cocaine on the viability of mosquito larvae when a solution of cocaine is applied to them. Percent adults surviving is graphed against cocaine concentration. At concentrations of as little as 0.01%, the percent larvae surviving to mature adulthood is approximately 50%. At 0.1%, no adults were produced.

The result of the application of a solution of cocaine to invertebrate larvae is shown in FIG. 11. The assay is described in the Methods section under "In vivo Methods—Method 3."

FIG. 11 is a graph of the effect of cocaine on the viability of mosquito larvae when a solution of cocaine is applied to them. Percent living adults is graphed against cocaine concentration. At concentrations of as little as 0.01%, the percent larvae surviving to mature adulthood is approximately 50%. At 0.1%, no adults were produced. A strong correlation between cocaine concentration and larvacidal activity of cocaine is demonstrated.

Example 7

Ovacidal Activity of Cocaine

Figure 12:
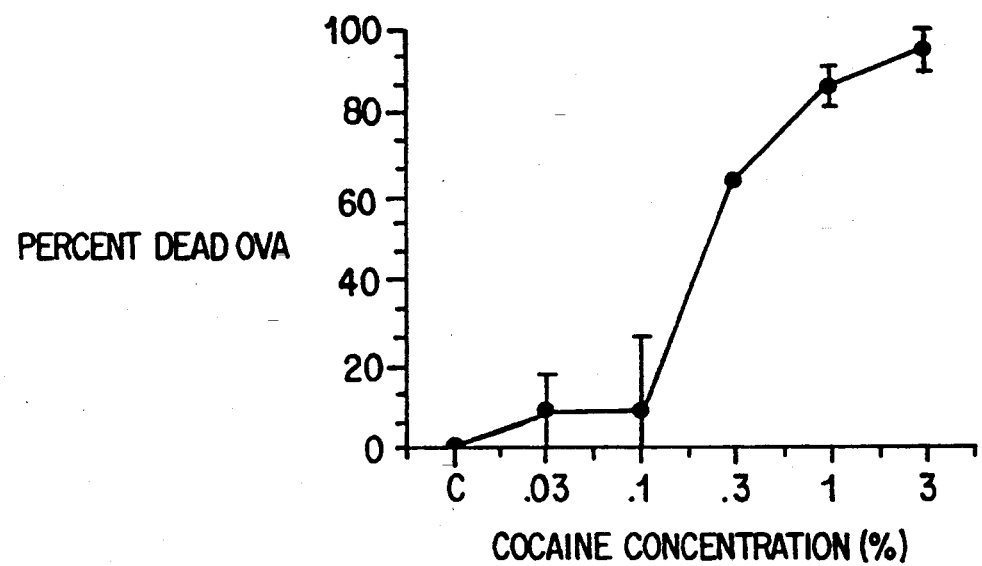
FIG. 12 is a graph of the effect of varying cocaine concentrations on the viability of M. sexta eggs. Percent dead ova are plotted against concentrations of cocaine ranging from 0 to 3%. At 3%, percent dead ova is greater than 95%. For the assay methods, see "In vivo Methods, Method 1".

The result of the application of a solution of cocaine to invertebrate eggs is shown in FIG. 12. For the assay methods, see "In vivo Methods—Method 1." FIG. 12 is a graph of the effect of varying cocaine concentrations on the viability of M. sexta eggs. Percent dead ova are plotted against concentrations of cocaine ranging from 0 to 3%. At 3%, Percent Dead Ova is greater than 95%. A strong correlation between cocaine concentration and ovacidal activity of cocaine is demonstrated.

Although the foregoing invention has been described by way of illustration and example for purposes of clarity and understanding, it will be obvious that certain changes and modifications may be practiced within the scope of the invention, as limited only by the scope of the appended claims.

We claim:

1. A method of controlling an invertebrate pest, comprising contacting said post with an effective pest-controlling amount of a 1,4-disubstituted piperazine having the formula

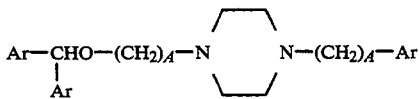

wherein:
Ar is independently phenyl which can be substituted by halogen, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, $C_3$–$C_6$ cycloalkyl, $C_2$–$C_6$ acyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl; and
A is independently 1 to 6.

2. The process of claim 1, wherein said 1,4 disubstituted piperazine is 1-(2-[bis-(4-fluorophenyl)methoxy]ethyl)-4-(3-phenylpropyl)piperazine (GBR 12909).

3. A process for inhibiting the feeding of an invertebrate pest comprising contacting said pest with an effective feeding-inhibiting amount of a 1,4-disubstituted piperazine having the formula

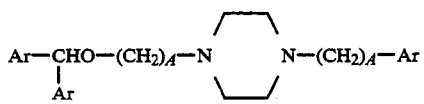

wherein:
Ar is independetly phenyl which can be substituted by halogen, $CF_3$, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, $C_1$–$C_6$ haloalkylthio, allyl, $C_3$–$C_6$ cycloalkyl, $C_2$–$C_6$ acyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl; and
A is independently 1 to 6.

4. The process of claim 3, wherein said 1,4-disubstituted piperazine is 1-(2-[bis-(4-fluorophenyl)methoxy]ethyl)-4-(3-phenylpropyl)piperazine (GBR 12909).

* * * * *